United States Patent
Caputo

(10) Patent No.: US 10,002,679 B2
(45) Date of Patent: *Jun. 19, 2018

(54) SYSTEM FOR BULK ENCODING MEDICAL ITEMS

(71) Applicant: MEPS Real-Time, Inc., Carlsbad, CA (US)

(72) Inventor: Jimmy C. Caputo, San Diego, CA (US)

(73) Assignee: MEPS Real-Time, Inc., Carlsbad, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/627,366

(22) Filed: Jun. 19, 2017

(65) Prior Publication Data

US 2017/0286602 A1    Oct. 5, 2017

Related U.S. Application Data

(63) Continuation of application No. 15/241,026, filed on Aug. 18, 2016, now Pat. No. 9,684,766.

(60) Provisional application No. 62/206,273, filed on Aug. 18, 2015.

(51) Int. Cl.
*G06F 19/00* (2018.01)
*G06K 7/10* (2006.01)

(52) U.S. Cl.
CPC ......... *G16H 10/65* (2018.01); *G06K 7/10366* (2013.01); *G16H 40/20* (2018.01); *G06F 19/3456* (2013.01)

(58) Field of Classification Search
CPC .............. G06F 19/3223; H04B 5/0062; G08B 13/2431; G06Q 20/352; H01Q 1/2216; H01Q 1/2225
See application file for complete search history.

(56) References Cited

U.S. PATENT DOCUMENTS

| | | | |
|---|---|---|---|
| 7,158,030 B2 | 1/2007 | Chung | |
| 8,346,632 B2 | 1/2013 | Saghbini | |
| 2003/0052788 A1 | 3/2003 | Chung | |
| 2007/0023513 A1* | 2/2007 | Andreasson | A61J 1/14 235/385 |

(Continued)

FOREIGN PATENT DOCUMENTS

| | | |
|---|---|---|
| JP | 2010052922 A | 3/2010 |
| KR | 100721972 B1 | 5/2007 |
| KR | 101276495 B1 | 6/2013 |

OTHER PUBLICATIONS

International Search Report from PCT/US2016/047657, dated Nov. 17, 2016, 3 sheets.

*Primary Examiner* — Kabir A Timory
(74) *Attorney, Agent, or Firm* — Thomas A. Runk; Brooks Kushman P.C.

(57) ABSTRACT

A system and method for bulk encoding medical items in a tracking system in a healthcare facility comprises attaching to each of a plurality of identical medical items a blank RFID tag. When activated simultaneously, the serial numbers of all RFID tags on all the identical medical items are read and their serial numbers are associated with the pre-stored characteristics of the medical item in a data base. The RFID tags are blank in that they include no human-readable data concerning the medical article to which the RFID tag is attached. A data mining system and method are provided for mining the database.

21 Claims, 15 Drawing Sheets

(56) References Cited

U.S. PATENT DOCUMENTS

2009/0309726 A1  12/2009 Fritchie et al.
2014/0184390 A1   7/2014 Elizondo, II
2015/0058182 A1   2/2015 Kress-Spatz et al.

* cited by examiner

| Search Query: | Name: | Concetration: | Quantity: |
|---|---|---|---|
| Most Encoded Drugs with Contraindications | Dopamine HCL | 40 mg/mL | 1,259 |
| | Ondansetron HCL | 2 mg/mL | 998 |
| Date: September 1, 2015 | ... | ... | ... |

SYSTEM FOR BULK ENCODING MEDICAL ITEMS

CROSS REFERENCES TO RELATED APPLICATIONS

This application is a continuation of U.S. application Ser. No. 15/241,026, filed Aug. 18, 2016, now U.S. Pat. No. 9,684,766, which claims the benefit of U.S. Provisional Application No. 62/206,273, filed Aug. 18, 2015, all of which are incorporated herein by reference.

BACKGROUND

The invention is related generally to a system and method for wirelessly tracking medical items through the use of RFID tags, and more particularly, for tagging and encoding medical items with RFID tags in a bulk manner.

Most medical items are produced with human-readable labeling that identifies the characteristics of the medical item so that it may be administered safely to a patient. For example, an administering nurse reads the label on the container of a tablet meant to be swallowed and determines from the label that the tablet in the container is 350 mg of a certain drug. The container may also have an expiration date for the tablet, a lot number, and other information. In other cases, the container may include the National Drug Code ("NDC") for the tablet and any applicable warnings. The U.S. Food and Drug Administration ("FDA") presently requires human-readable labeling. Such labels are typically attached to containers of medication with adhesive before the container leaves the manufacturer. Because of the adhesive, they can be difficult to remove. Due to FDA regulations and the adhesive used, they are considered to be integral with the medical item and the container.

Title 21 of the Code of Federal Regulations presents a comprehensive scheme for human-readable drug labeling. Medical items falling under the jurisdiction of the Food and Drug Administration must be labeled in a certain way to satisfy the laws and regulations. Following the regulations results in medical items that can be clearly identified simply by reading their integral labels. However, attempting to track medical items in a healthcare facility by means of visually reading the label of each medical item is impractical.

Automation has been developed in this area. For example, RFID systems have been developed to assist in tracking medical items from their receipt at a healthcare facility through the administration of the medical item to a patient. RFID systems have resulted in a great benefit to healthcare facilities in that medical items can be tracked wirelessly. However, an RFID transponder (also referred to as an RFID "tag") must be attached to the medical item to enable this system to function and must also be associated with data about the medical item to which the RFID tag is attached.

Read-only RFID tags are often used and each has a unique serial number (according to their manufacturers) that is used to identify the tag. When the read-only RFID tag is activated, it transmits its unique serial number. In the case of read-only RFID tags, a database of some type is needed to then correlate the serial number of an RFID tag with the medical item to which it is attached. Read-only RFID tags are manufactured in enormous quantities and are relatively inexpensive.

Writable RFID tags also exist. These tags not only include a unique serial number but also include a memory of a certain size to which data can be written. When these writable RFID tags are activated in the "write" mode, data about the medical item to which they are attached can be written to their memories. When activated and controlled to be in the "read" mode, the RFID tags transmit their unique serial number and the data stored in their memories. In some cases, a unique serial number for a writable RFID tag may not be needed. Writable RFID tags are more expensive than read-only RFID tags.

The FDA has been aware of RFID systems and in 2004 it published the FDA Compliance Policy Guide ("CPG") § 400.210 which addressed the use of RFID tags attached to drugs. This document provided general guidance by the FDA in 2004 that RFID will be used only for inventory control, tracking, and tracing of products. RFID will not be used in lieu of current labeling control systems. The tags will contain a serial number that uniquely identifies the object to which the tag is attached. The addition of the RFID tag will not block, obscure, or alter any of the product's existing and approved label and labeling information. The RFID tag will not substitute for, replace, or interfere with a linear bar code required pursuant to 21 CFR § 201.25. This latter requirement would provide the ability to identify the drug when electronic means are unavailable.

Many healthcare facilities purchase large quantities of medical items to be administered to their patients. Those medical items are received at the healthcare facility from manufacturers, distributors, or repackagers and have the human-readable labeling on them as required by the FDA. Because there is no FDA requirement for the attachment of an RFID tag by a manufacturer, distributor, or repackager, many of these received medications are delivered to the healthcare facility without one. If the facility desires to track these delivered medical items through the use of an RFID system, it must attach the RFID tags itself while bearing in mind the above-listed FDA policy guidance that the human-readable labeling should not be blocked, obscured, or altered by attachment of the RFID tag.

In many healthcare facilities, automation of medical item tracking has been put in place because of the many benefits it provides. Where that system comprises the use of RFID tags on medical items, the contents of a medical item and its characteristics, including those characteristics relevant to safety of use, are typically stored in a computer database. The RFID tags placed on the medical items are in many cases read-only devices that transmit only their individual serial number when they are read. The RFID tracking system associates that RFID tag serial numbers with the information in the database pertaining to the medical item to which the RFID tag is attached and thereafter, when the tracking system reads the serial number of the RFID tag attached to the medical item, the computer will identify the medical item information thereof. The tracking system generally prescribes that medical items are to be immediately tagged with RFID tags and associated with database data as soon as possible after arrival at the healthcare facility. A problem can arise when the serial number of the RFID tag is associated with the wrong data in the database when this initial tagging operation is performed.

FIGS. 1 and 2 show one technique for attaching an RFID tag 10 to a drug vial 12 that is in use presently. FIG. 1 shows the front of the vial and FIG. 2 shows the back. The vial 12 includes an integral human-readable label 14 containing FDA-required printed information about the contents of the vial. A second label 16 is attached to the vial 12 with clear adhesive tape 18. On the front side 20 of the second label 16 shown in FIG. 1, human-readable information copying that on the integral label 14 is present on a printable area 21 of the tag. On the back side 22 of the second label 16 shown in FIG. 2, only the mounted RFID tag 10 exists. It can be noted that the front side 20 of the second label 16 has identical information (drug name, NDC, manufacturer name, and expiration date) as some of the information of the integral FDA-mandated label 14. Unfortunately, if the human-readable information on the second label 16 does not match that on the integral first label 14, the inconsistency can lead to a medical error.

Furthermore, the second label 16 of FIGS. 1 and 2 was printed with the information from the integral label 14 on the printable area 21 of the first side 20 before the label 16, which includes the RFID tag 10, was attached to the vial 12. If the RFID tag 10 had been read after printing but before it was attached to a vial, and its serial number then associated with a vial in a computer database at the healthcare facility, a problem could develop if that second label 16, along with its RFID tag 10, is then attached to the wrong vial. In such a case, a medical error could occur.

It is believed that in the above procedure, a plurality of second labels are printed before attaching any of them to a vial. This may be considered to be a bulk encoding technique in such a case. To be successful, this procedure requires that the correct second labels be attached to the correct vials. Human effort is required in comparing the second labels to the integral labels before attaching the second labels. Such a procedure can be prone to error, as mentioned above.

Similar encoding of the serial numbers of RFID tags to data stored in a database can be beneficial in other areas in which medical items are tracked. Manufacturers, repackagers, and distributors of medical items all may need to attach RFID tags to medical items and encode those RFID tags to a database or databases. In such cases, bulk encoding could greatly improve the speed of encoding the RFID tags and its accuracy.

Hence those of skill in the art have recognized a need for an RFID tag tracking system that results in more accurate tagging and data association. In the medical field, a need has been recognized for accurately encoding RFID tags to the correct medical item and for avoiding errors in attaching RFID tags to medical items. A need exists for avoiding second labels that have human-readable information printed thereon that could be inconsistent with an integral label on same medical item due to human error. Another need has been recognized for avoiding the association of the wrong serial number of an RFID tag with data in the database. Yet a further need exists for encoding multiple items simultaneously to increase the speed of encoding, yet reducing the chances for errors in encoding. The present invention fulfills these needs and others.

SUMMARY OF THE INVENTION

Briefly and in general terms, the present invention is directed to a system that reduces the risk of errors that may occur in an RFID system used to track medical items in a healthcare facility. In one method aspect in accordance with the invention, there is provided a method for labeling a medical item received at a healthcare facility with an RFID tag for identifying and tracking the received medical item while in the healthcare facility, comprising receiving a medical article having a name and characteristic related to safety of use of that item, storing information about the received medical article, including the name and the characteristic related to safety of use, in a computer-readable database located in a non-volatile memory, attaching a blank RFID tag to the medical item, the RFID tag having a serial number, after the blank RFID tag has been attached to the medical item, reading the blank RFID tag while attached to the medical item to obtain the serial number of the RFID tag attached to the medical item, and associating the serial number read from the RFID tag when it was attached to the medical item to the name and characteristic related to safety of the medical item in the database thereby uniquely identifying that medical item with the RFID tag serial number.

Characteristics related to safety of use of a medical article or medical item include, but are not limited to, a National Drug Code (NDC) associated with the medical item, a lot number, an expiration date, dose, concentration, patient identifiers identifying a patient intended to receive the medical product, administration requirements, instructions for use, product warnings such as possible allergic reactions or adverse interactions of the medical item with other medical products, and contraindications. Contraindications indicate situations when a certain drug should not be given to a patient because the drug may be harmful to the patient due to the patient's physical or physiological conditions (e.g. the patient is using other specified drugs, the patient has a temperature above a certain threshold, etc.) or due to the drug's environmental conditions (e.g. the drug is not refrigerated, the drug was not refrigerated between a certain temperature range, the drug was removed from refrigeration longer than a specified timeframe, etc.). For example, a contraindication for the drug dopamine may state that the drug should not be used in patients with pheochromocytoma, with uncorrected tachyarrhythmias, or ventricular fibrillation. Moreover, a contraindication for the drug ondansetron may state that the drug should not be concomitantly used with apomorphine. Other examples of contraindications for various drugs may state that a drug should not be used if the patient is pregnant, if the patient has a fever with a temperature over 101 degrees Fahrenheit, if the drug was not refrigerated between 2 and 8 degrees Celsius, if the drug was removed from refrigeration for over 3 hours, or other similar physical, physiological, or environmental conditions.

In more detailed aspects, the method further comprises attaching the RFID tag to the medical item in a way that does not obscure the human-readable information on a label of the medical item. Additionally, attaching the RFID tag to the medical item comprises adhering the RFID tag to the medical item with a material that is clear thereby allowing text on the human-readable label to be read through material such that when attached to the medical item over the human-readable information, the human-readable information is not obscured.

In yet further method aspects, the step of receiving comprises receiving a plurality of identical medical items, the step of storing information comprises storing the name and characteristics that are identical for all of the received medical items, the step of attaching comprises attaching a separate blank RFID tag to each of the plurality of received medical items, each blank RFID tag having a different serial number, the step of reading comprises reading all RFID tags that are attached to the received medical items together, the step of associating comprises first checking that all names and characteristics of the plurality of received, RFID-tagged, and database-entered medical item information of all the plurality of medical items are the same before associating each of the read RFID tag serial numbers to the information stored in the database.

Turning now to system aspects, there is provided a system for use by a healthcare facility to track a medical item that was received by the healthcare facility and to which an RFID tag having a serial number was attached to the medical item at the healthcare facility for use in identifying and tracking the received medical item in the healthcare facility, the system comprising a blank RFID tag attached to the medical item wherein the blank RFID tag has no human-readable information located thereon related to the medical item, a nonvolatile memory device in which is stored a database of information including information about the received medical item, the information including a characteristic related to safety of use of the received and RFID-tagged medical item, an RFID reader that transmits activation energy to the RFID tag attached to the medical item in response to receipt of a read control signal and that reads the serial number of the RFID tag transmitted by the RFID tag in response to the receipt of the activation energy, the RFID reader providing the received serial number, and a processor programmed to communicate a read control signal to the RFID reader to have the RFID reader read the RFID tag attached to the medical item, and the processor further programmed to receive the serial number of the read RFID tag and to communicate with the memory device to store that received serial number in the database, and further to associate the stored serial number with the stored information of the medical item, including the stored characteristic of the medical item related to safety.

More detailed aspects include the system is also for tracking a plurality of medical items, each of which has the same characteristics related to use and each of which has a blank RFID tag attached, comprising bulk encoding RFID tags with medical items, wherein the blank RFID tag attached to each of the medical items has no human-readable information located thereon related to the contents of a medical item, a nonvolatile memory device in which is stored a database of information including information about the received medical items, the information including characteristics related to safety of use of the received and RFID-tagged medical items, an RFID reader that transmits activation energy to the RFID tags attached to the medical items in response to receipt of a read control signal and that reads the serial numbers of each of the RFID tags transmitted by the RFID tags in response to the receipt of the activation energy, the RFID reader providing the received serial numbers, an input device configured to receive information and that communicates that information in response to input device control signals, a display device that visually displays information in response to display control signals, and a processor programmed to receive an input signal to read RFID tags, the processor further programmed to control the display to communicate a requirement to input a signal confirming that all medical items whose tags are to be read have identical characteristics related to use, the processor further programmed so that in the event that it receives input data confirming that all medical articles whose tags are to be read have identical characteristics related to use the programmer will communicate a read control signal to the RFID reader to have the RFID reader read the RFID tags attached to the medical items, the processor further programmed to receive the serial numbers of the read RFID tags and to communicate with the memory device to store those received serial numbers in the database, and further to associate the stored serial numbers with the stored information of the medical items, including the stored characteristic of the medical item related to safety, the processor further programmed that in the event that it does not receive input information confirming that all medical items whose RFID tags are to be read are identical, to control the display device to recommend that the medical items that are not identical with the others be removed from the reader.

A more detailed system aspect comprises the programmer being further programmed when controlling the display to request confirmation further to control the display to ask about the medical items to be read at least one of the following: if all medical items to be read have the same lot number, if all items to be read have the same expiration date, if all medical items to be read have the same dosage, if all medical items to be read have the same concentration, and if all medical items to be read have the same manufacturer.

Yet another aspect in accordance with the invention is a data mining system and process by which characteristics of medical items stored in the non-volatile memory are "data mined" using various search requests through a processor, an input device, with the results provided by the processor at an output device.

The features and advantages of the invention will be more readily understood from the following detailed description that should be read in conjunction with the accompanying drawings.

DETAILED DESCRIPTION OF THE PREFERRED EMBODIMENTS

Figure 3:
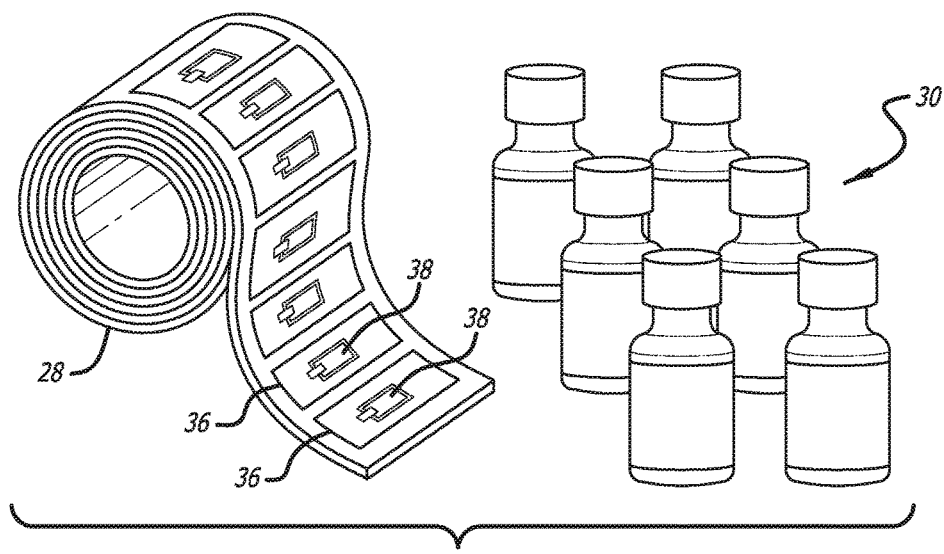
FIG. 3 is a depiction of a roll of blank RFID tags, each of which has a substrate on which is mounted an RFID circuit which has a unique serial number, for attaching to medical items received at a healthcare facility. The medical items in this figure are shown as being six vials each containing a pharmaceutical. While each of the RFID tags have an RFID circuit, none have any human readable text that pertains to any medical item to which they may be attached, i.e., they are "blank;"

Referring now in more detail to the exemplary drawings in which like reference numerals designate corresponding or like elements among the several views, FIG. 3 shows a roll of RFID tags 28 and a plurality of medical items 30. Each of the RFID tags 36 on the roll includes an RFID circuit 38 having a unique serial number that will be used for identifying and tracking a medical item 30 to which the tag is attached. In the case where the medical items arrive at a healthcare facility without RFID tags attached to them, an RFID tag will be applied to them. Pharmacy personnel will store information about each of the medical items to which the tags are attached into a computer-readable database located on a non-volatile memory. Then, before any encoding of the RFID tags takes place, pharmacy personnel will attach the RFID tags to the medical items shown in FIG. 3. An example of a medical item with an attached RFID is shown in FIG. 4.

It should be noted that only two RFID tags on the roll of tags 28 of FIG. 3 are designated with the reference numerals 36 (tag) and 38 (RFID circuit). However, these reference numerals are meant to apply to every one of the RFID tags and RFID circuits on the roll. Drawing reference numerals pointing to all labels on the roll have not been used so as to preserve the clarity of the figure.

Figure 1:
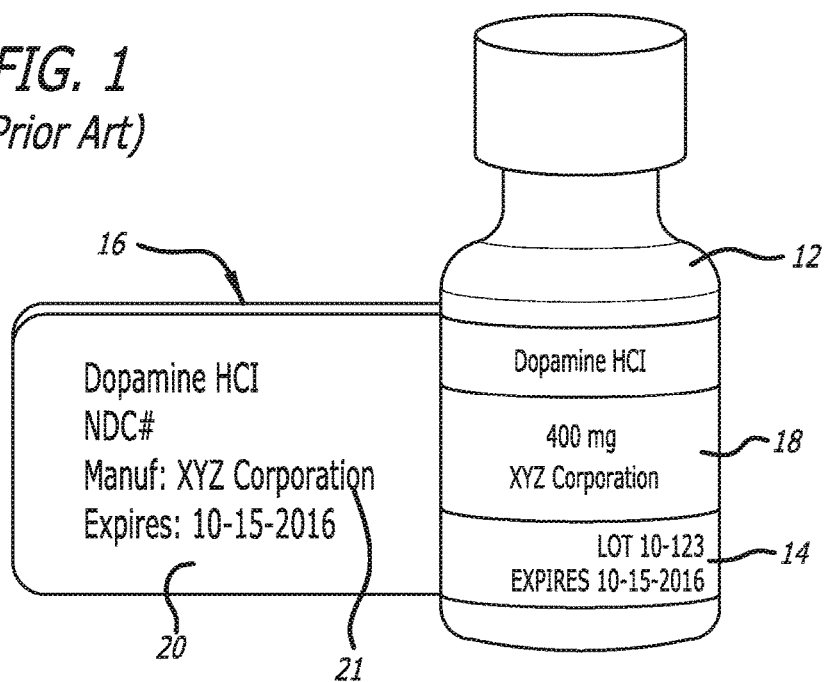
FIG. 1 is a perspective view of a prior art medical item, in this case a medication vial, having an integral human-readable label mounted on the vial itself and a second label attached to the vial with clear adhesive tape, the second label including a printable area having human-readable text on one side and an RFID tag on the opposite side, this view showing the front side of the attached second label with the human-readable text visible.
Figure 2:
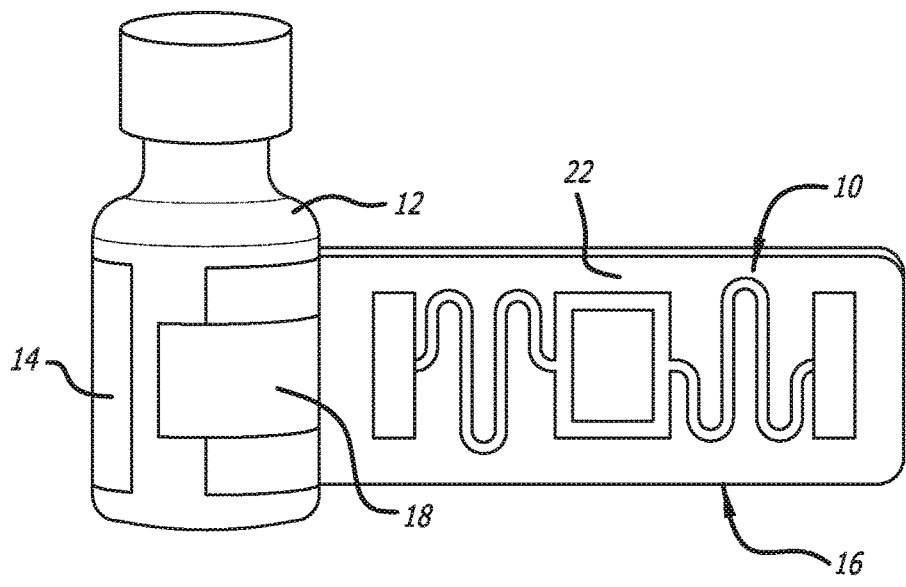
FIG. 2 is a second view of the same prior art vial shown in FIG. 1 but shown from the back side so that the RFID tag can be seen on the back side of the attached second label.
Figure 4:
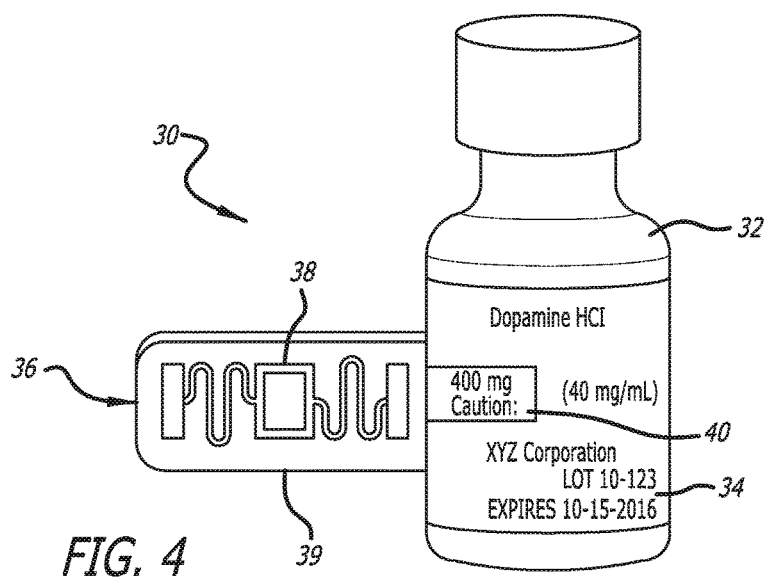
FIG. 4 shows an RFID tag in accordance with aspects of the present invention in which a blank RFID tag is attached to the medication vial, the blank RFID tag having no human-readable text that relates to the contents of the vial, but instead is only a blank tag containing only an RFID circuit.

FIG. 4 shows an RFID-tagged medical item 30 in accordance with aspects of the invention. In particular, the medical item 30 comprises a vial 32 in which is stored a liquid drug named Dopamine HCl. The vial also has an integral FDA-mandated label 34 in human-readable form having information such as the name of the contents, the concentration, the volume, the manufacturer, the lot number, and the expiration date. The label 34 is typically attached firmly to the medical article or the container in which the medical article is stored with adhesive or adhesive tape so that it will not fall off under normal handling conditions. It is considered to be the integral label of the medical item. Additional or less information may be included as required. The RFID tag in this case is indicated by drawing numeral 36 and includes an RFID circuit 38 mounted on a substrate 39. In one embodiment, no human-readable writing exists anywhere on the RFID tag 36, including the substrate, in the example shown in FIG. 4. As in the example shown in FIGS. 1 and 2, the RFID tag 36 of FIG. 4 is attached to the vial 32 through means of clear adhesive tape 40. Because the tape is clear, the human-readable information printed on the integral label 34 of the vial is not obscured or blocked and is clearly readable, as indicated by the FDA in the guidance document of 2004 discussed above. FIG. 4 shows that the printing on the integral label 34 can be read through the adhesive tape 40. In particular, the numbers and words "400 mg, caution" can be read clearly. Because of this advantageous arrangement in which a blank RFID tag 36 is used, there will be nothing readable on the RFID tag that is inconsistent with any information printed on the integral human-readable label 34 of the vial and one possible source of a medical error has therefore been eliminated.

Figure 5:
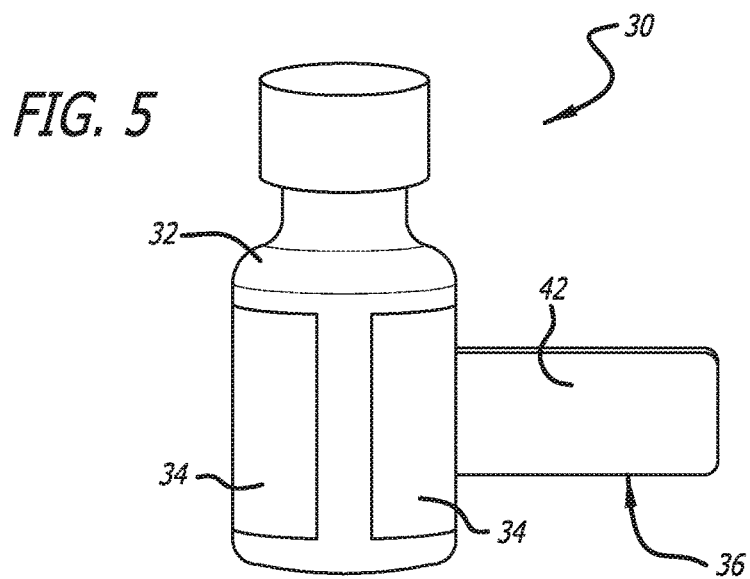
FIG. 5 is a back view of the vial of FIG. 4 showing that the back of the blank RFID tag includes a substrate but that substrate contains no human-readable matter.
Figure 6:
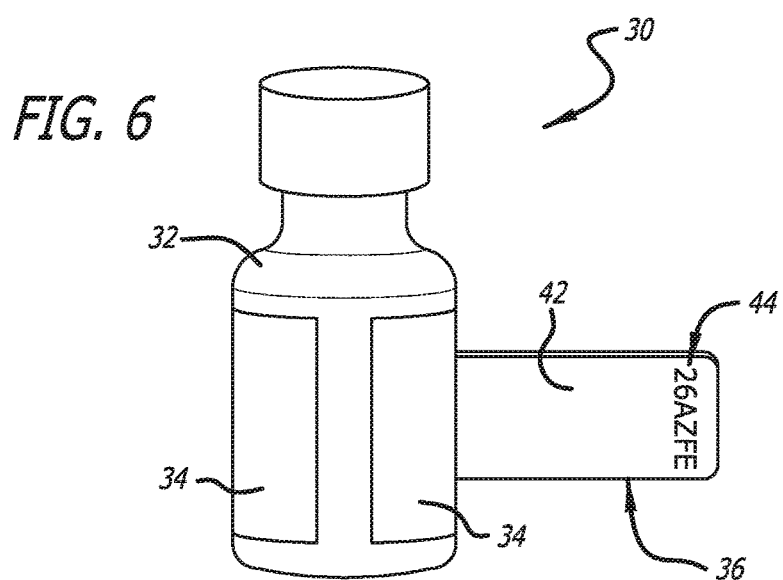
FIG. 6 is also a back view of the vial of FIG. 4 showing that the back of the blank RFID tag in this embodiment includes a substrate but on the substrate of this figure is printed six characters in human-readable form ("26ZAFE") which are the last six characters of the serial number of the RFID circuit mounted on the substrate on the opposite side. However, the six characters printed on the tag are not related to the contents of the vial, they are only related to the RFID circuit that is attached to the vial.
Figure 7:
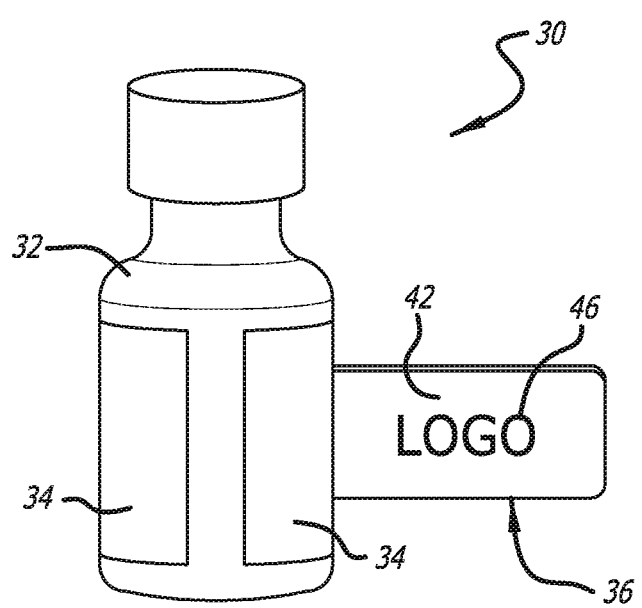
FIG. 7 is yet another back view of the vial of FIG. 4 showing that the back of the blank RFID tag includes a substrate on which is printed a logo for the RFID tag, but the logo shown is also not related to the contents of the vial.

Turning now to FIGS. 5-7, three back views of the vial 32 of FIG. 4 are shown. All three examples of RFID tags shown in FIGS. 5-7 are considered to be "blank" RFID tags since the tags do not include human-readable information related to medical article characteristics or to the container in which the medical article is stored and to which the RFID tags are attached. In the case of FIG. 5, it will be seen that the back 42 of the RFID tag 36 has no writing whatsoever. In FIG. 6, the back 42 of the RFID Tag 36 includes the six characters 44 which are "26A2FE." These are the last six characters 44 of the serial number of the RFID electronic device mounted to the other side of the RFID tag. These six characters are unrelated to any characteristic of the medical item to which the RFID tag is attached or to the container of the medical article to which the RFID tag is attached. Also, these six characters do not relate to any information concerning the medical article that is printed on the integral label 34. They therefore cannot be inconsistent with any of the integral label 34 of the vial 32. Expressed another way, if any writing did exist on the blank RFID tag 36, it would not be related to the medical article or the contents of the container of the medical item 30 to which the RFID tag 36 is attached. Any writing on an RFID tag would be related to something else.

Similarly, in FIG. 7, the back of the RFID tag includes a logo 46 which, in this case is the trademark Intelliguard® with the three arches design. Manufacturers or distributors may desire to place a logo on the RFID tag to show their brand. Like the representation of part of the serial number of the RFID tag in FIG. 6, the logo 46 in FIG. 7 is unrelated to the medical article and is not related in any way to the printed material on the integral human-readable label 34 of the vial.

Figure 8:
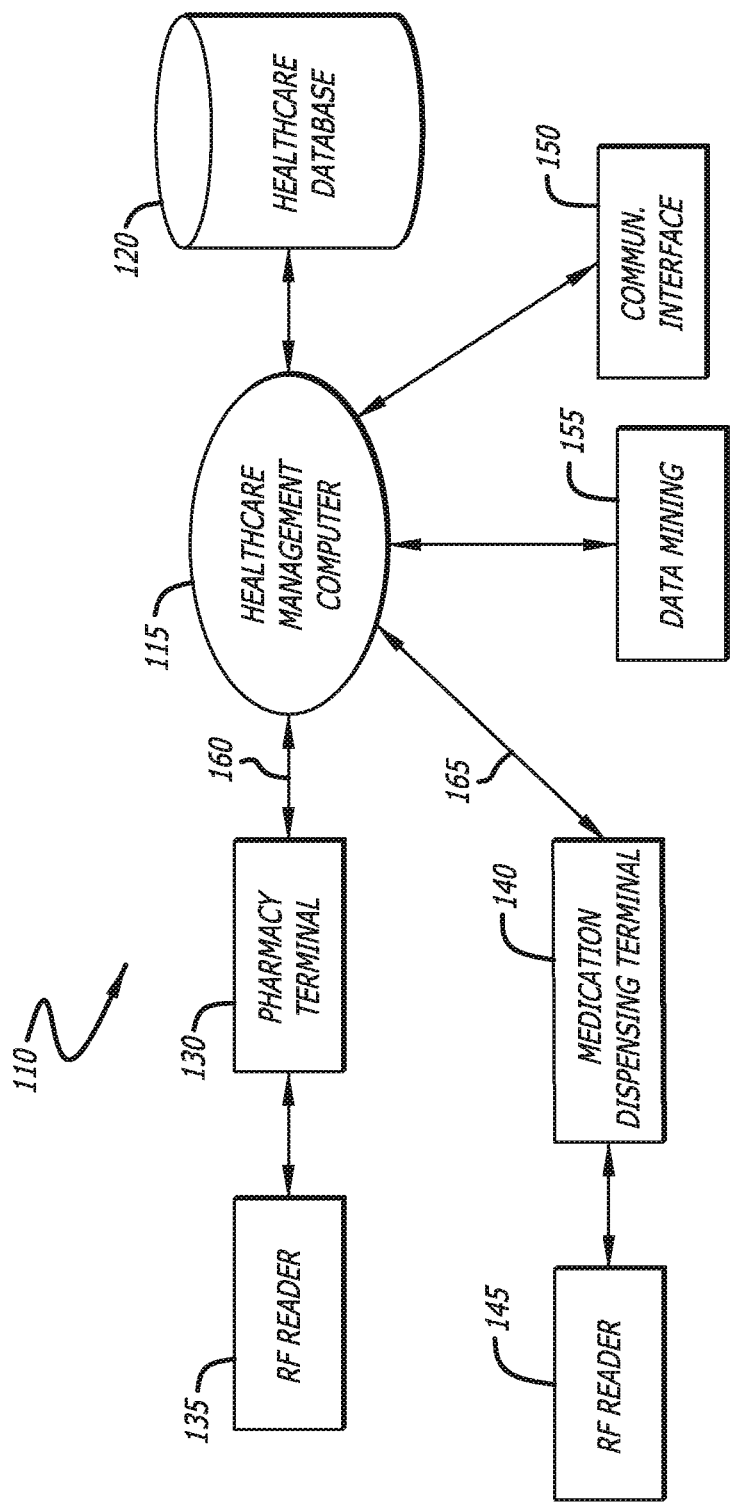
FIG. 8 is a diagram illustrating a system for tracking and monitoring medical products having a healthcare management computer (which is also referred to herein as a processor), a nonvolatile memory device in which is stored a healthcare database where identifying information about medical items is stored and may be accessed by the healthcare computer, a pharmacy terminal (also referred to as a computer or processor) connected with an RF reader, a medication dispensing terminal (also referred to as a computer or processor), connected also to an RF reader, a communications interface for wired and/or wireless connection of the healthcare management computer to remote sites, and a data mining system for mining data stored in the healthcare database.

FIG. 8 is a diagram illustrating a system 110 for tracking and monitoring medical items. The system 110 may be implemented at a healthcare facility, such as a hospital, a secondary or long-term care facility (e.g. a nursing home), a clinic, a physician's office (e.g. a neurologist's office where the neurologist stores specific drugs to be encoded and tracked), or other facility or location where medical items are tracked. Alternatively, the system 110 may be implemented outside the healthcare facility, such as at a distribution facility, a manufacturing plant, or the like. The system 110 includes a healthcare management computer 115 and a healthcare database 120 stored in a non-volatile memory. The healthcare management computer 115 is also referred to herein as a processor and is programmed to manage, retrieve, and store information related to the operation of the healthcare facility in the healthcare database 120. The management computer 115 may take different forms, such as a central computer and/or a network of computers, a desktop, laptop, tablet, or other computer or computers, and may or may not be physically located on the premises of the healthcare facility. The system 110 also includes a pharmacy terminal 130 coupled to a RF reader/writer 135 and a medication dispensing terminal 140 coupled to a RF reader 145. Each of the terminals 130 and 140 preferably includes a processor, memory, an input device, and an output device such as a display (all of which are not shown) for performing the tasks described below. The use of RFID tags and RF readers allow individual medical products to be scanned and also allow larger quantities, such as boxes or trays, of medical products to be scanned at once (in bulk). Thus, the products can be read at any appropriate station, namely, the pharmacy and dispensing terminals, and others. Additionally, the system 110 includes a communications interface 150 through which the healthcare management computer 115 can communicate with a remote location external from the healthcare facility or even within the healthcare facility but in a different location. For example, where the healthcare management computer 115 is located in a healthcare facility, the communications interface 150 allows the healthcare management computer to communicate remotely with a manufacturer or distributor, or external data storage residing elsewhere, such as in the "cloud." Moreover, the system 110 includes a data mining system 155 that enables a pharmacy technician, manufacturer, distributor, or any other person or entity to mine data related to the information stored in the healthcare database 120. More details related to the data mining system 155 are described below with reference to FIGS. 16-18.

In addition, each of the RF readers 135 and 145 may be built into their respective terminal 130 and 140. Each of the terminals 130 and 140 are linked to the management computer 115 via communications links 160 and 165 respectively. The communications links 160 and 165 may take different forms such as cable links, optical links, and/or wireless links, e.g., short-range RF links. Preferably, each of the terminals 130 and 140 is programmed to access patient and/or medical item information stored in the healthcare database 120 via the communications links 160 and 165. The healthcare database 120 may be located at the same facility as the medical items or may be located elsewhere, such as in the "cloud." The healthcare database may be divided up among multiple memory devices that may be located in different locations.

Although denoted as "terminals" 130 and 140 above, these devices may take many forms and the designation of being a "terminal" is not meant to be limiting. They can take the forms of laptop computers, desktop computers, tablet computers, smart phones, and other devices that have the ability to receive, process, store, and output data.

The information stored in the healthcare database 120 includes a patient file in this embodiment that is uniquely associated with each individual patient admitted in the healthcare facility. Each of the patient files includes the patient's name, address, social security number, and/or patient ID, which may be assigned to the patient upon admission to the healthcare facility. Each of the patient files also includes the medical items prescribed to the respective patient and/or a record of the medical items administered to the respective patient, including dates and time of administration, the healthcare worker who administered the medical items, and other information as needed or desired. Each of the patient files also includes the current location of the patient within the healthcare facility, e.g., the floor and/or room number of the patient in the healthcare facility for example. The information in the database 120 further includes insurance billing information for each individual patient, including the name, telephone number, billing address, and/or group ID of the patient's insurer. In addition, the information in the database 120 includes a healthcare worker file associated with each individual healthcare worker who is working at the healthcare facility. In one embodiment, each of the healthcare worker files includes reports reflecting the work performance of the healthcare worker, as explained further below. Additional or other information may be stored in the database 120.

Furthermore, the healthcare database 120 in this embodiment is used to store data about all medical items brought into the healthcare facility. The medical items are tracked within the healthcare facility by attaching a radio frequency identification (RFID) tag to them as shown and discussed above. An RF reader is used for reading the serial number stored in the RFID tag by transmitting an RF interrogation signal to induce the RFID tag to transmit its information to the RF reader. The RFID tag may be active, i.e., powered by an internal power source, or passive, i.e., powered by a RF interrogation signal transmitted from the RF reader.

The healthcare database 120 in one embodiment also stores various other information related to the medical items brought into the healthcare facility. In one embodiment, the information includes a National Drug Code (NDC) associated with the medical item, an item name, a manufacturer's name, a lot number, and an expiration date. The information in the database also includes dose information, identifying the amount and/or concentration of the medical item, and/or a patient identifier identifying a patient intended to receive the medical product. Other optional information includes administration requirements, instructions for use and/or product warning, such as possible allergic reactions or adverse interaction of the product with other medical products, and contraindications. Additionally stored in the database 120 are links (also described as "associations") of the RFID tag serial numbers with certain data stored in the database.

Figure 9:
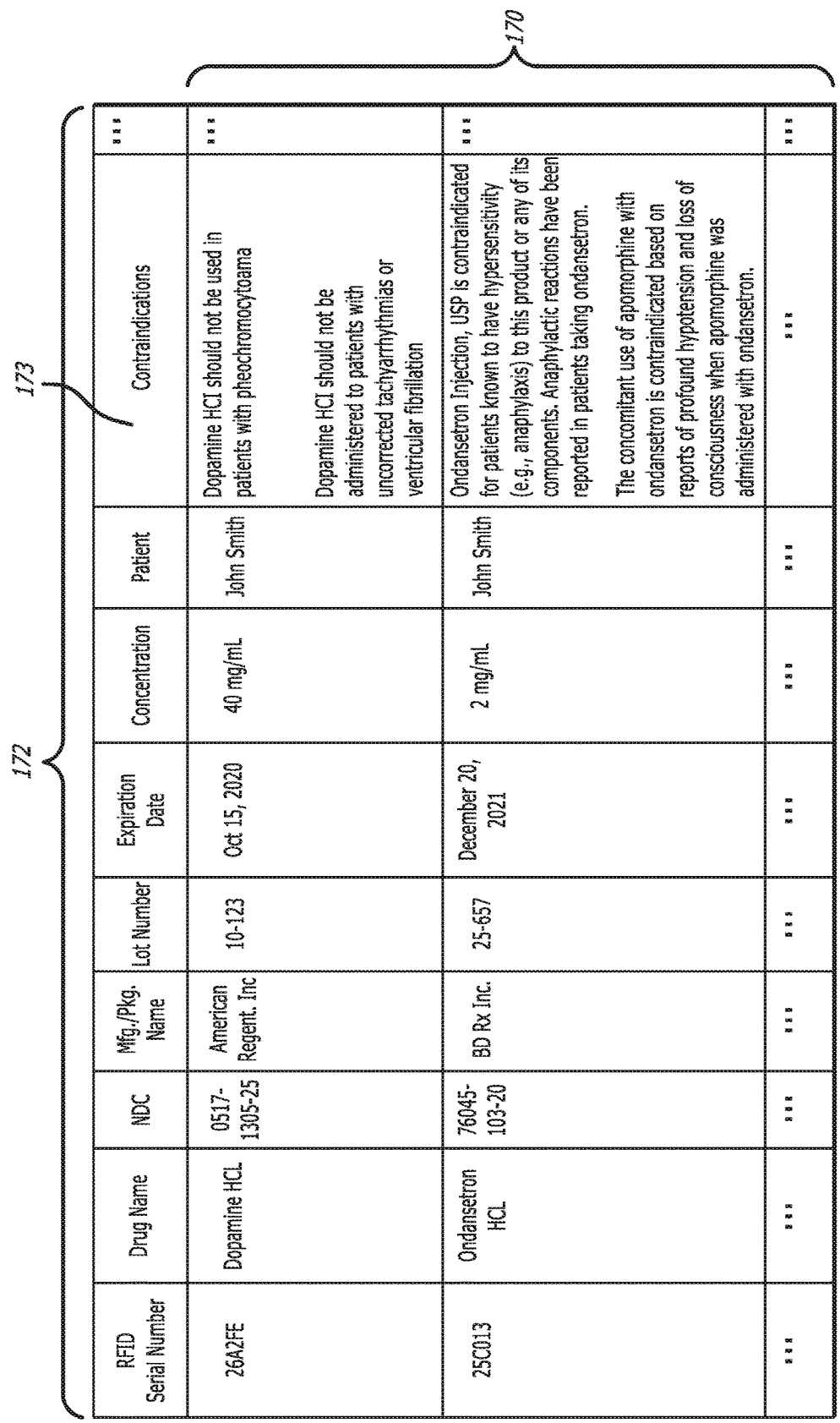
FIG. 9 is a depiction of exemplary data which takes the form of stored records in the healthcare database illustrated in FIG. 8; examples of identifying information about medical items including drugs that include, but are not limited to a part of the serial number of the RFID tag attached to the drug, the name of the drug, the NDC, the drug manufacturer or packager's name, the lot number, the expiration date, the dose or concentration amount, the patient to which the drug is assigned, and any contraindications for the drug.

FIG. 9 shows examples of stored records of information 170 in a healthcare database 120 and RFID tag links. In this drawing, there are multiple columns 172 describing data elements and each row 170 relates to a tagged medical item. Each record of information 170 preferably includes a representation of the RFID tag serial numbers (e.g. the last six digits) and the drug name and characteristics of use related to safety 173 of the medical items associated or linked with the RFID tag serial numbers. Characteristics 175 contained in healthcare database 120 include, but are not limited to, the drug name, the NDC of the drug, the manufacturer or packager's name, the lot number, the expiration date, the concentration, the patient to which the drug is assigned, and any contraindications of the drug. The last row contains multiple ellipses indicating the existence of additional data.

As used in regard to the embodiments herein, "tag" is meant to refer to an RFID transponder as well as a substrate on which the transponder is mounted. Such tags typically have a coupling element, such as an antenna, and an electronic microchip. The microchip includes a processor and data storage, also referred to as memory. Each of the RFID tags may be made thin and flexible, allowing the RFID tag to be attached to most medical items such as a delivery device (a syringe for example), medical container (vial for example), and/or packaging (not shown) so that the RFID tag does not interfere with using the delivery device. In some cases, the RFID tag may be taped to the medical item with clear adhesive tape so as not to obscure human-readable information written on the label that is adhered to the medical item or its container.

RFID tags offer several advantages over conventional barcode tags. For example, an RF reader does not require a line of sight between itself and a RFID tag to read the information in the RFID tag. In addition, an RF reader may read many RFID tags at a time, while a barcode reader or scanner can only read one barcode tag at a time. Furthermore, RFID tags are smaller, more accurate, more durable, and some are capable of storing more information than barcode tags.

As used in regard to the embodiments herein, "reader" and "interrogator" refer to a device that may read or read and write to an RFID tag. A data capture device is always referred to as a reader or an interrogator regardless of whether it can only read or is also capable of writing. A reader typically contains a radio frequency module (a transmitter and a receiver, sometimes referred to as a "transceiver"), a control unit, and a coupling element (such as an antenna or antennae) to the RFID tag. Additionally, many readers include an interface for forwarding data elsewhere, such as an RS-232 interface. The reader, when transmitting, has an interrogation zone within which an RFID tag will be activated. When within the interrogation zone, the RFID tag will draw its power from the electrical/magnetic field created in the interrogation zone by the reader, referred to as activation energy.

In a sequential RFID system (SEQ), the interrogation field is switched off at regular intervals. The RFID tag is programmed to recognize these "off" gaps and they are used by the tag to send data, such as the tag's unique identification number also referred to interchangeably as its serial number. In some systems, the tag's data record contains a unique serial number that is incorporated when the tag is manufactured and which cannot be changed. This number may be associated in a database with a particular article when the tag is attached to that article. Thus, determining the location of the tag will then result in determining the location of the article to which it is attached. In other systems, the RFID tag may contain more information about the article to which it is attached, such as the name or identification of the article, its expiration date, its dose, the patient name, and other information. The RFID tag may also be writable so that it can be updated.

Figure 10:
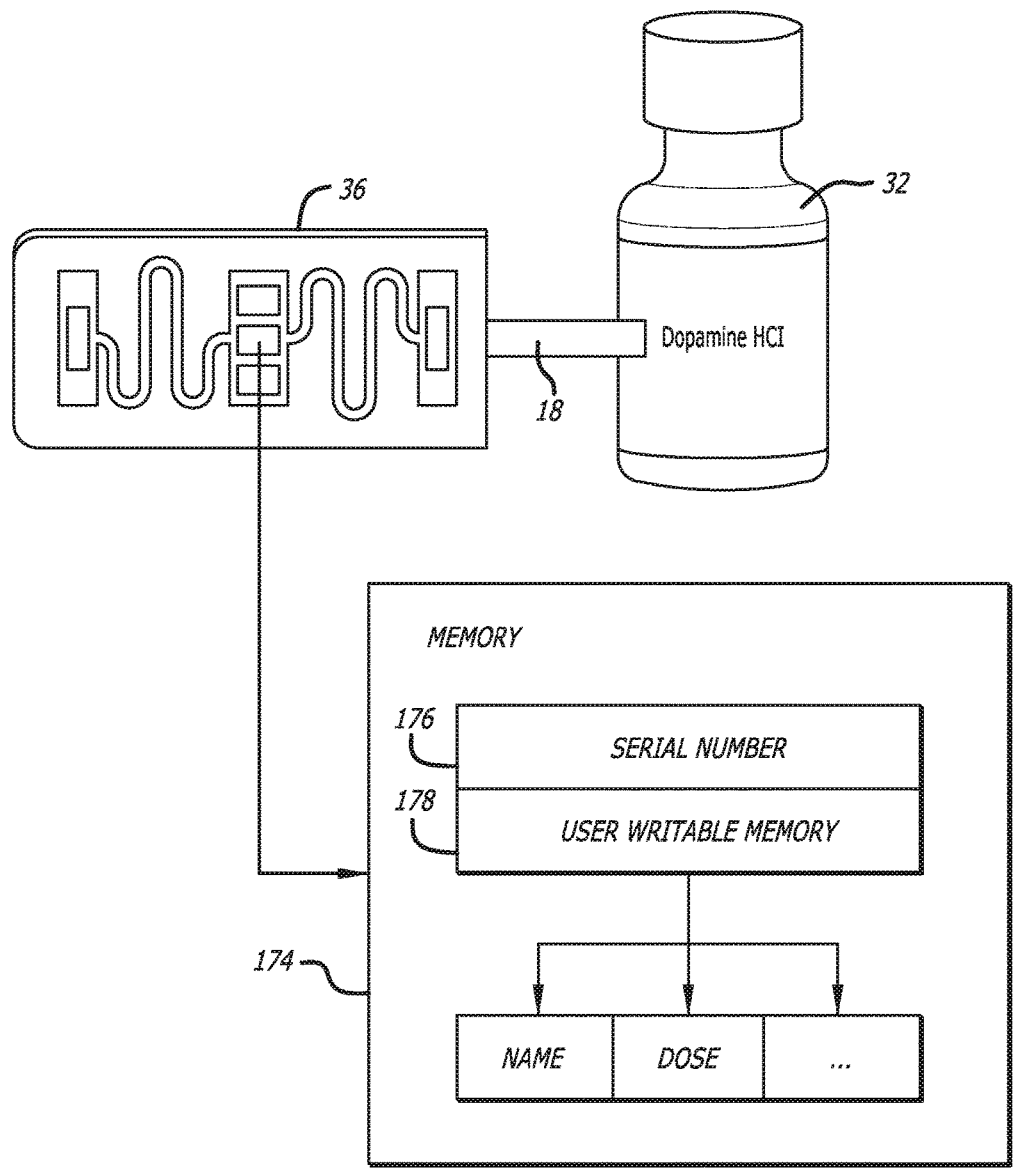
FIG. 10 is a block diagram of a medical item, in this case a vial, having an RFID tag attached thereto, the RFID tag including a memory that stores a unique serial number for the RFID tag and to which a user may write additional data, such as the name and characteristics of use related to the medical item to which the tag is attached.

FIG. 10 illustrates an embodiment of a writable RFID tag 36 that includes a memory 174 that stores a serial number 176 identifying the RFID tag, and additional blocks of data or user-writable memory 178 for storing information related to the medical item 32 to which the RFID tag is attached. This drawing is not to scale and is not meant to provide details of the elements other than a block diagram thereof. In this case, the RFID tag is attached by clear adhesive tape 18. For example, user-writable memory 178 may be used to store the name and characteristics of use related to safety of the medical item 32 to which the RFID tag 36 is attached. In particular, the memory 174 of the writable RFID tag may include the name of the medical item, its concentration, its expiration date, its dose, contraindications, or other characteristics of use.

Figure 11:
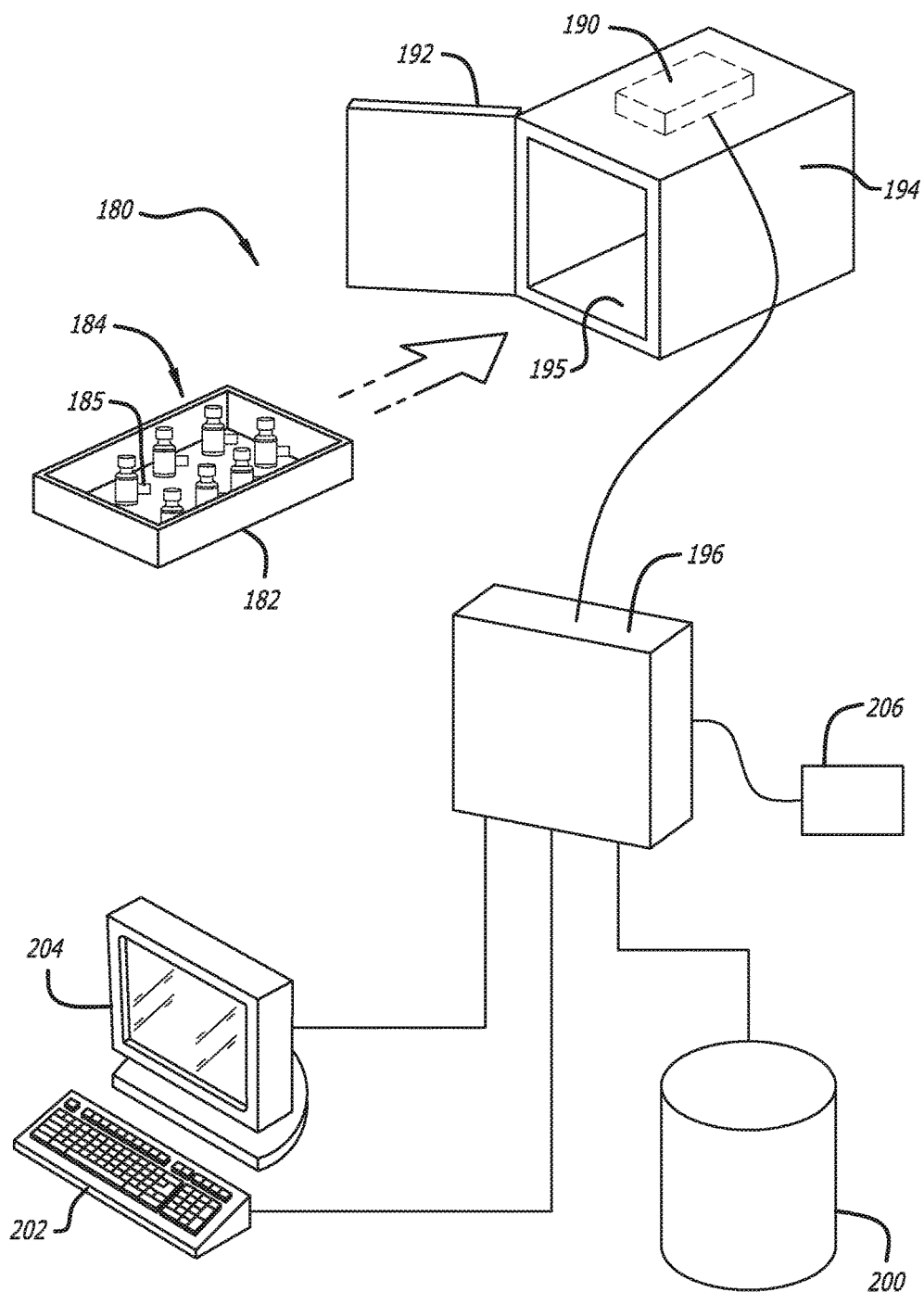
FIG. 11 is a block diagram of an embodiment of a tracking system in accordance with aspects of the invention in which a plurality of identical medical items, each of which has a blank RFID tag attached to it, are to be bulk encoded, wherein the RFID tags attached to the medical items in the tray are read by an RFID reader in bulk and the individual serial numbers of the read RFID tags are stored by a processor into a database.

Referring now to FIG. 11, a system 180 for bulk encoding medical articles in accordance with aspects of the invention is shown. A tray 182 of medical items 184 (indicated collectively by drawing numeral 184), each of which is identical with all others in the tray, has been prepared for bulk encoding. Each medical item has had a blank RFID tag 185 attached to the item. No human-readable printing pertaining to any characteristics of the medical item exists on the RFID tags 185 in this embodiment. However, each medical item 184 retains its manufacturer's integral attached label.

An RFID reader 190 is readied to read all the RFID tags 185 of the medical items 184 in the tray 182. The reader in this embodiment is located within an enclosure 194 (thus the reader is shown in dashed lines), the interior reading space 195 of which is isolated from the outside environment with either a Faraday-type cage (not shown) or the enclosure contains RF absorptive material throughout so as to confine the reader to reading only those RFID tags within the enclosure. The enclosure further has a door 192 that is shown in the open configuration. The door is also configured to form a part of a Faraday cage or includes RF absorptive material for isolation purposes of the interior reading space 195. The interior reading space is large enough to receive trays and other containers that hold pluralities of RFID tagged medical items for bulk encoding. The electronics, power, communication, and processor controls of the RFID reader 190 are not shown nor are they described herein since they are well known to those of skill in the art and such readers are available commercially.

The tray 182 of medical items 184 should be checked to verify that each medical item has a blank RFID tag attached and each medical item is identical with all others in the tray. By "is identical" is meant that in the case of drugs, each medical item is the same drug, with the same dose, the same expiration date, etc. The pharmacy may decide fi two drugs are identical if they are made by different manufacturers and encode them together, of they may be encoded separately. If all medical articles are identical, the tray is then be inserted into the interior reading space of the reader 190 and the door 192 closed. Although a tray is illustrated in this embodiment, other types of containers may be used instead.

A processor 196 is then used to perform the bulk encoding. In this case, the processor includes programming so that it controls the RFID reader 190 and receive the serial numbers of the RFID tags read by the RFID reader. FIG. 11 shows the processor 196 connected to a non-volatile memory device 200 that has a medical item database stored thereon. Programming instructions for the processor are stored on the non-volatile memory 200 or in another embodiment, may be located elsewhere, such as in a non-volatile memory of the processor itself, or may be run remotely. The processor is also coupled to an input device 202, in this case a keyboard, and an output device 204, in this case a visual display device. The processor 196 is further connected to other processors or memories or other devices through a communication interface 206 through wireless or wired means. The communication interface may connect to the Internet, or to internal or external networks or to all as is required for the tracking system 180. In accordance with a different embodiment, the memory device is located in the "cloud" and the processor must communicate with it through the communication interface 206 over the Internet or use another route.

In one embodiment, the memory device 200 includes a database of identifying data about the medical items 184 in the tray that was created before the RFID tags of the medical items 184 are read by the RFID reader 190. In another embodiment, the database information may be stored by other means. The database of identifying data can come from multiple sources. In one case, the manufacturer of the medical item may furnish a database about those medical items. In another case a distributor may prepare and furnish a database and in yet another case, a secondary repackager may prepare and furnish a database. In the embodiment herein, a pharmacy member manually enters the data concerning the medical items into the database by keyboard or other data input means.

If everything is in order, the processor 196 will then communicate with the RFID reader 190 and control it to read all RFID tags 185 within the interior reading space 195, which will be all of the tags on the medical items 184 in the tray 182, and report those RFID tag numbers to the processor. The processor will then associate all those RFID tag serial numbers with the relevant medical item data previously stored in the database 120 stored in the memory 200. Control over this process is managed by the programmed processor as may be controlled by the keyboard 202 and the display 204.

As is used herein, "encoding" is directed to linking the serial numbers of the RFID tags on the medical items to data stored in a database that pertains to the medical items. Where the RFID tag is on a container of a medical item, such as a medicinal fluid, the RFID tag is linked in the database to that medical fluid. In the case where the RFID tag is on a medical item itself, such as a pair of surgical shears, the database stores information about those shears.

Where writable RFID tags are used in system 180, the system operates similarly as described above except that some or all of data concerning the medical item to which the RFID tag is attached may be written onto the writable RFID tags so that such data can be read directly from the RFID tag itself, if needed. In one embodiment, that data would be written to the tag during the encoding process. Once data is written to the writable RFID tag, it may be locked so that the written data cannot be changed. This may occur automatically by built-in means of the writable RFID tag, or an external signal may be needed to accomplish this. This use of writable RFID tags could have a significant advantage should access to a database be disrupted for some reason. Depending on what data is stored in the writable RFID tag, operations of tracking medical items through the healthcare facility could continue. Although at the present date writable RFID tags are much more expensive than those that are read-only, this may change in the future.

Although FIG. 11 demonstrates an embodiment where the RFID tagged medications 184 are bulk encoded at the healthcare facility, the encoding may also take place outside of the healthcare facility. In other embodiments, the RFID tagged medications are bulk encoded at a manufacturing or distributing facility before being transported to the healthcare facility. In such a case, the encoding facility would provide the ultimate customer with the database that links the serial numbers of the RFID tags to the data about the medical items to which the RFID tags are attached.

Figure 12:
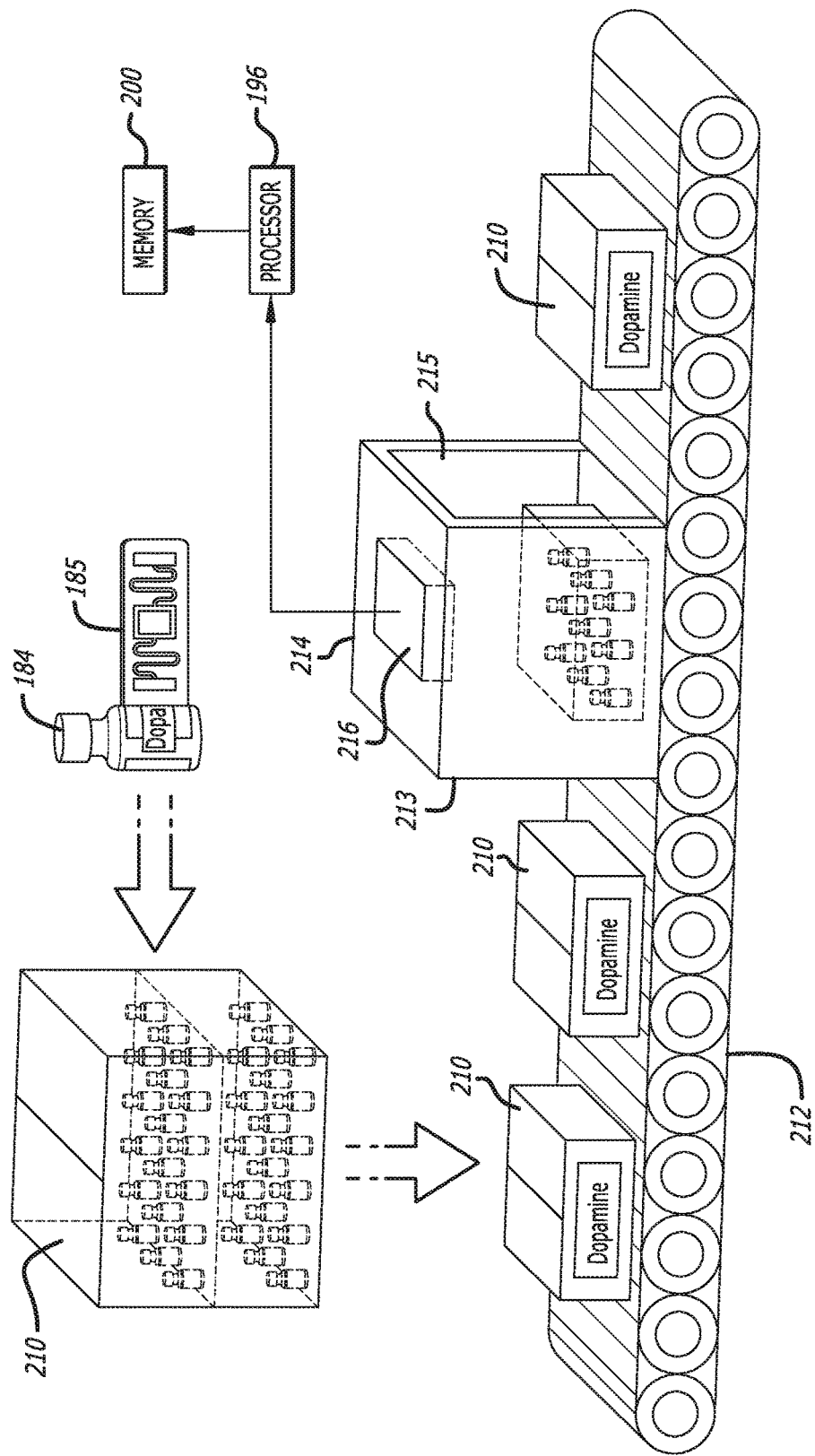
FIG. 12 is a block diagram of an embodiment of a bulk encoding system according to aspects of the present invention in which a plurality of identical medical items, each having a blank RFID tag attached to it, are bulk encoded while on a conveyor belt using an RFID reader that reads the serial numbers of the tags simultaneously as the items travel down a conveyor belt, and that communicates the serial numbers read from the tags to a processor to be stored in a database and linked to identifying information about the medical items.

In another embodiment as shown in FIG. 12, an RFID reader 216 may be positioned in an enclosure 214 that is located over a conveyor belt 212 for bulk encoding medical items 184 as they travel down the conveyor belt. Afterwards, the medications are transported to the healthcare facility. Blank RFID tags 185 are affixed to a plurality of identical medical items 184. The tagged medical items are subsequently placed in a box 210 or other container for shipping multiple medical items, and the box is then placed on the conveyor belt. The conveyor belt carries the box of medical items to a bulk encoding enclosure 214 that has an RFID reader 216 as part of it. A programmed processor 216 controls the RFID reader 216 to simultaneously read the serial numbers of all of the plurality of the RFID tags in the box when it is positioned within the bulk encoding enclosure. The serial numbers read by the RFID reader 216 are communicated to the processor 196 which associates or "links" the serial number of each RFID tag 185 with the identifying information related to the medical item 184, to which the tag is attached, stored in the database 120 located on the non-volatile memory 200.

The enclosure 214 in one embodiment includes RF absorptive material to prevent the RFID reader 216 from reading any RFID tags of medications in boxes other than the one in the enclosure. Alternatively the boxes 210 are sufficiently spaced apart on the conveyor belt 212 such that inadvertent tag readings do not occur. Although not shown, flaps may be used at the inlet 213 and outlet 215 openings of the bulk encoding enclosure 214. These flaps may contain electrically conductive material that connects with a shield within the bulk encoding enclosure to lessen the amount of RFID frequency electromagnetic energy being transmitted outside the enclosure by the RFID reader and being received within the enclosure from RFID tags that are not within the enclosure. RF absorptive material incorporated into the flaps may also be used.

Figure 13:
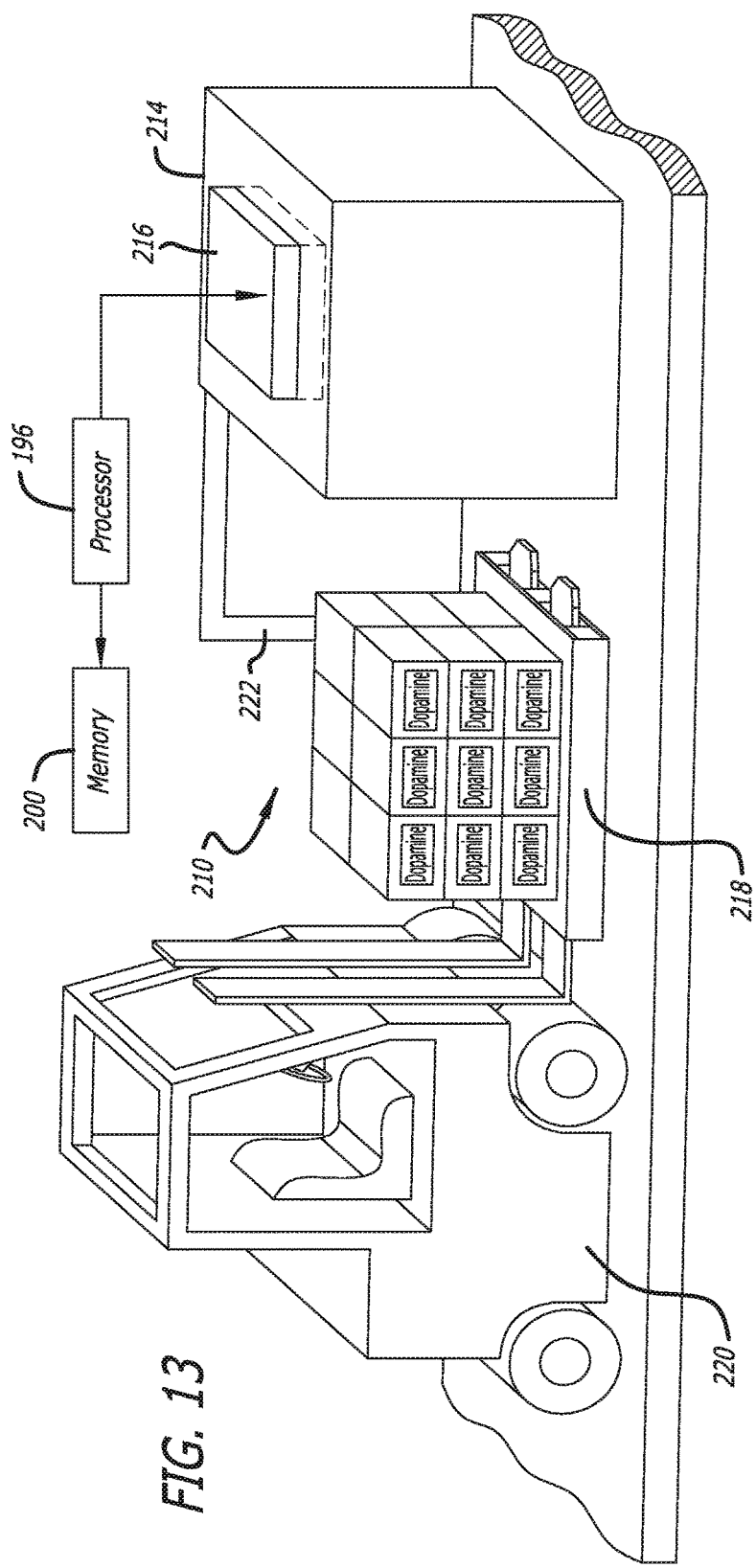
FIG. 13 is a block diagram of an embodiment of a bulk encoding system according to aspects of the present invention in which a plurality of identical medical items, each of which has a blank RFID tag attached to it, are bulk encoded while on a pallet, wherein the pallet is placed inside a large RFID reader enclosure by a forklift in this example, and the RFID reader in the enclosure reads the serial numbers of the RFID tags for storage in a database that links them to the medical items.

Alternatively as shown in FIG. 13, bulk encoding may take place after the boxes of medications 210 have been placed on a pallet 218 and transported inside a bulk encoding enclosure 214 having an RFID reader 216 attached. As was done with FIG. 12, blank RFID tags 185 were affixed to a plurality of identical medical items 184. The tagged medical items are also placed in boxes 210; however in this embodiment, stacks of multiple boxes 210 are placed on a pallet 218 instead of a conveyor belt. A forklift 220 moves the pallet of stacked boxes of medical items to a bulk encoding enclosure 214. The enclosure 214 has an RFID reader attached as in FIG. 12. In one embodiment, the enclosure either includes a Faraday cage type of structure within it to contain electromagnetic energy within and resist electromagnetic energy from without, or includes RF absorptive material to lessen the risk of EM escaping the bulk encoding enclosure or getting into the enclosure. The RFID reader simultaneously reads the serial numbers of all of the plurality of the RFID tags on all medical items in all the boxes on the pallet once the pallet is fully positioned within the enclosure. In this case, the enclosure 214 includes a door 222 which is also fitted as part of a Faraday cage or also has RF absorptive material mounted to it. The serial numbers read by the RFID reader are communicated to the processor 196 which associates them with the identifying information related to the medical items stored in a database 120 located on the non-volatile memory 200. Subsequently, the pallet of the encoded medical items and the database are transported to a healthcare facility.

Figure 14:
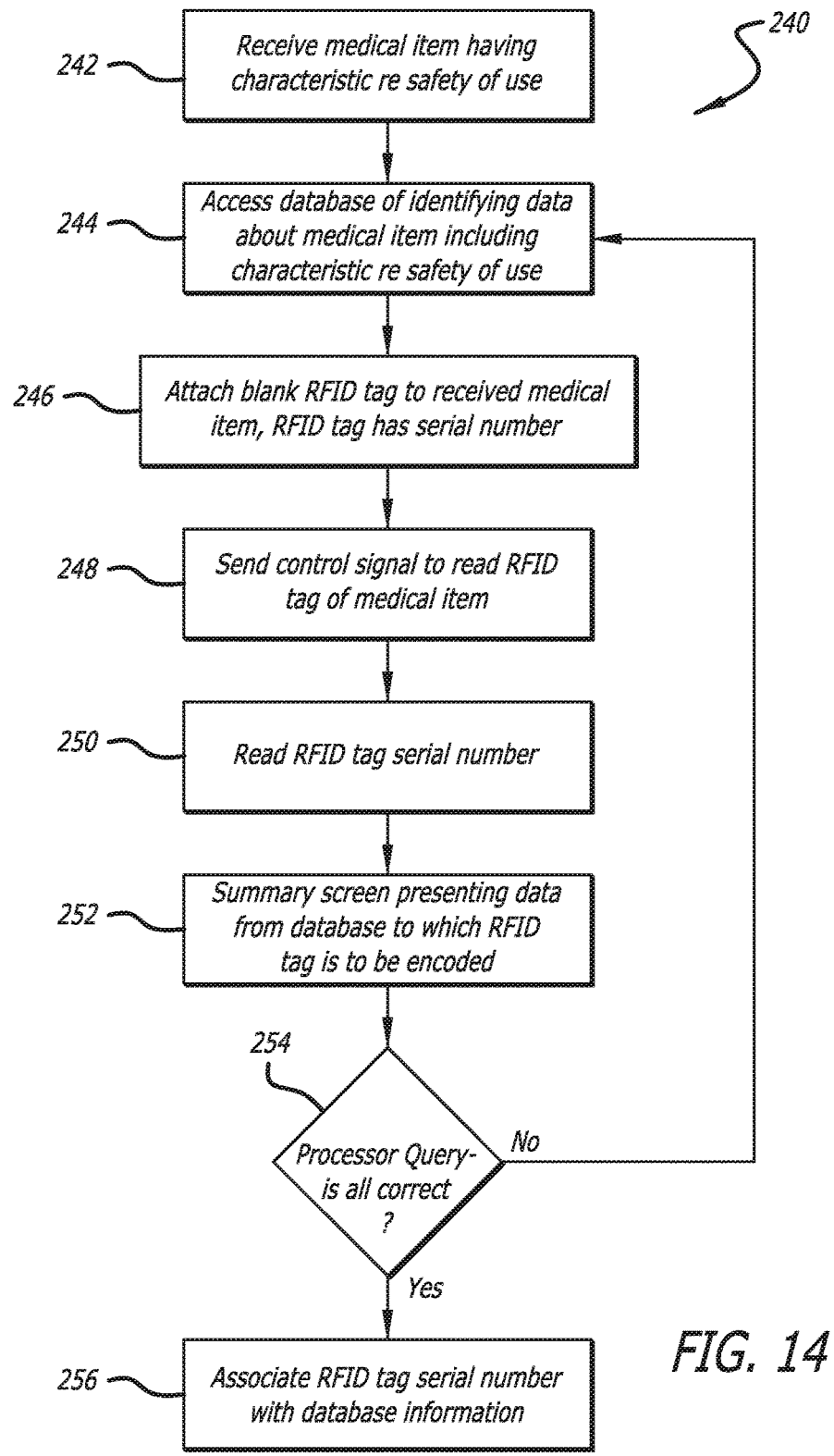
FIG. 14 is a diagram showing the operation of a computer program in accordance with aspects of the invention in which a medical item has a blank RFID tag attached, is then read, and the serial number of the blank RFID tag attached to the medical item is associated with a database having identifying data of the contents or the substance of the medical item.
Figure 15:
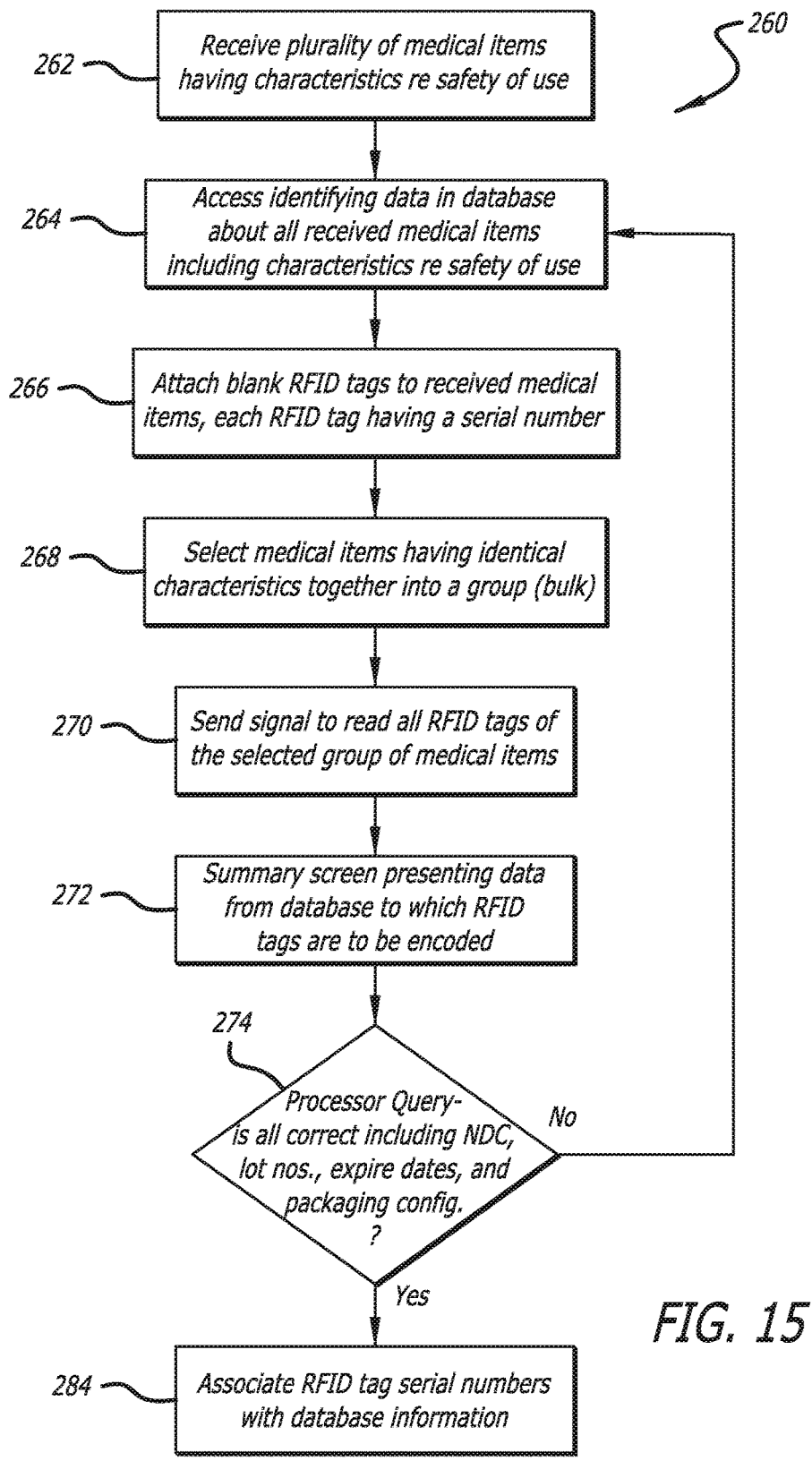
FIG. 15 is a diagram of the operation of a computer program in accordance with aspects of the invention in which a plurality of identical medical items are grouped together for bulk encoding in which each of the plurality of the medical items has a blank RFID tag attached to it before it is read by an RFID reader, the computer program causing a reader to read all RFID tags in bulk and then associate the serial numbers of the read RFID tags with data stored in the database.

Further programming details of the processor 196 and method aspects in accordance with the invention are shown in FIGS. 14 and 15. Turning now to FIG. 14, a method 240 for encoding the serial number of an RFID tag is shown. A medical item is received 242 and relevant characteristics may be the name of the drug, concentration, dose, expiration date, and others. Identifying data about the medical item is stored in a database stored in a memory device and that database is accessed 244. Storing data in the database may be done by manual entry, by receiving a storage device from a manufacturer and copying files into the local database, by connection over a web to reach the details, or by other means. A blank RFID tag is then attached to the medical item 246. An example of this is shown in FIG. 4 and described above. The RFID tag is blank when it has no human-readable information on it that pertains to the contents of the medical item. For example, some forms for preparing RFID tags include a printable area 21 on the opposite side of the tag, such as that shown in FIGS. 1 and 2. In one example, the manufacturer of the RFID tag form prints a representation of the last six characters of the serial number on the RFID tag. Because these last six characters have no relation to the contents of the medical item on which the RFID tag will be attached, the RFID tag is considered to be blank. Similarly, if the manufacturer of the RFID tag form prints a logo on the RFID tag, the RFID tag is still blank since the logo has no relation to the contents of the medical item on which the RFID tag will be attached.

In the next step of the method, an operator of a tracking system sends a command to the processor to read the RFID tag of the medical item 248 and the reader reads the serial number of the RFID tag 250. The processor is programmed to display a summary screen 252 in which the data to be associated with the read RFID tag serial number may be associated. The operator may check the NDC, the lot number, the expiration date, the packaging configuration and any other aspects of the medical item. If the data matches the medical item whose RFID tag has just been read, the operator may press a YES button or otherwise signify YES. The programming then causes the computer to associate the read RFID tag's serial number with the data on the Summary Screen 256. However, if the data on the Summary Screen does not match the medical item whose RFID tag was just scanned, the operator may then press a NO button or otherwise signify NO and the program will return to the second step 244 of accessing the database. In other embodiments, an NO answer may cause the program to return to other steps in the process.

FIG. 15 presents a method 260 in accordance with aspects of the invention in which a plurality of medical items are bulk encoded with the medical item database and their individual RFID tag serial numbers. A plurality of medical items are received at the healthcare facility 262. The medical item database stored in a nonvolatile memory device is accessed 264 for identifying information about the medical items articles just received. Each of the received medical items has a blank RFID tag 266 attached to it. An example of such an attachment is shown in FIG. 4. Each of those RFID tags has a serial number that the tag will transmit upon being activated.

Instead of activating each of the RFID tags individually and associating each tag separately with the database (encoding) as was done in FIG. 14, in accordance with this embodiment, bulk encoding is performed. Because all RFID tags that are used are blank, any tag can be attached to any medical item. Then, the medical items are inspected and those that are identical to one another are selected and moved together in a group 268 into an RFID reader, such as the reader 190 shown in FIG. 11. The operator then provides an input to the processor to read the RFID tags of the group of medical items in the reader 270.

In accordance with one embodiment, the processor displays a Summary Screen 272. The summary screen 272 displays the data to be associated with the read RFID tags' serial numbers. The operator may check the NDCs, the lot numbers, the expiration dates, the packaging configurations, and any other aspects of the medical items that have been read. If the data matches the medical items whose RFID tags have just been read, the operator may press a YES button or otherwise signify YES. The programming then causes the computer to associate the read RFID tags' serial numbers with the data on the Summary Screen 274. However, if the data on the Summary Screen does not match the medical item whose RFID tag was just scanned, the operator may then press a NO button or otherwise signify NO and the program will return to the fourth step 268 of selecting medical items having identical characteristics for bulk encoding. In other embodiments, an NO answer may cause the program to return to other steps in the process.

Figures 16, 17:
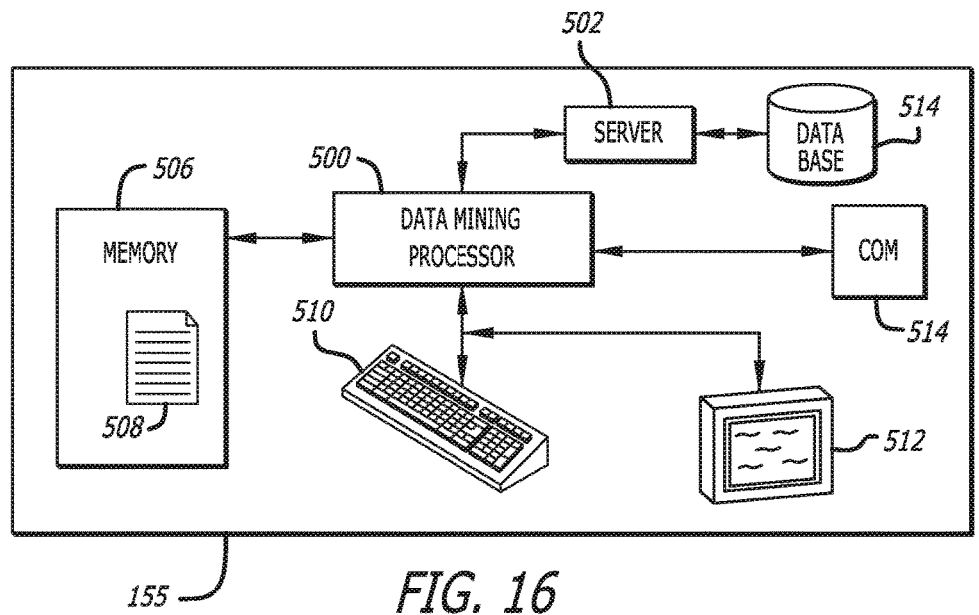
FIG. 16 is a block diagram of an embodiment of an encoding and tracking system according to an aspect of the present invention that includes a data mining system, wherein a processor is in communication with a memory on which is stored a list of data mining programming instructions, a server on which is stored a database containing identifying information for the tagged and encoded medical items, an input device in which data mining search queries are input to the processor, a display device in which data mining results are displayed, and a communications interface through which data mining results are externally communicated from the healthcare facility.
FIG. 17 is a depiction of exemplary data mining results displayed on the display device or communicated from the healthcare facility via a communications interface in response to a data mining search query.

Referring to FIG. 16, in a further preferred embodiment of the present invention, the system 110 includes a data mining system 155 in communication with the health management computer 115 (see FIG. 8). The data mining system 155 includes a processor 500 in communication with a server 502. In one embodiment, the health management computer 115 (FIG. 8) serves as the processor 500; alternatively, the processor 500 may be an additional processor separate from health management computer 115. The server 502 has mounted thereon a database 504 that includes identifying information for the medical items. Such identifying information includes the name of the medical items as well as other characteristics of the medical items. Such characteristics may include the NDC, the lot number, the expiration date, dosage, etc. In one embodiment, the database 504 is the same as the healthcare database 120 (FIG. 8).

The processor 500 is also in communication with a memory 506. On the memory 506 is preferably stored a program or list of data mining instructions 508, which include instructions to be mined by processor 500 in the database 504. The processor 500 is also in communication with an input device 510 such as a keyboard, a display device 512 such as a monitor, and a communications interface 514 that externally communicates with a remote location such as a manufacturer or distributor outside of the healthcare facility.

The processor 500 is configured to communicate with the memory 506 and the database 504 upon control by the input device 510. For example, upon receipt by input device 510 of a data mining search query to mine for and obtain data from database 504 about characteristics related to safety of use of medical items, processor 500 accesses identifying information from database 504 including the names and characteristics of medical items. After processor 500 accesses the information from database 504, processor 500 analyzes the accessed information in response to the search query submitted. The processor 500 then reports results from its analysis of the information accessed from the database 504 by sending an output signal to the display device 512 to visually display content depicting the results. Alternatively, processor 500 reports results from its analysis outside the healthcare facility to a remote location via communications interface 514.

Additionally, processor 500 is configured to receive search queries from the list of data mining instructions 508 in memory 506 rather than input device 512. First, input device 510 receives a signal to mine for and obtain data from the database 504 about characteristics related to safety of use of the medical items. Upon receipt of this signal, processor 500 runs program 508 in memory 506 and obtains each data mining search query from the list of data mining instructions 508. The data mining system 155 then operates identical as described above until the search queries in the list have all been run, including accessing identifying information from database 504, analyzing the accessed information in response to each search query, and reporting the analysis of information for each search query by transmitting an output signal to the display device 512. The results reported are preferably grouped by each individual search query; alternatively, the results reported may display all search queries combined.

FIG. 17 illustrates an example of reported results 516 based on analysis of a particular search query. The data mining system 155 reports on the display device 512 a table of the data mining results. In one exemplary embodiment of results 516 reported to the display device 512, the report includes the data mining search query that the processor 500 received, for example, "Most Encoded Drugs With Contraindications". The report also preferably includes the date of the search query, namely when it was run by the processor 500, and the identifying information of the medical items considered in the analysis. For example, report 516 includes the names of drugs analyzed, the concentration or dosage of each drug, and the quantity of each drug.

For example, a pharmacist may attempt to mine data in the data mining system 155 to determine the most encoded drugs with contraindications. As illustrated in FIG. 17, the system may report, for example, that dopamine and ondansetron are the most encoded drugs with contraindications thus far with over 1200 drugs of dopamine and almost 1000 drugs of ondansetron have been encoded on Sep. 1, 2015. Other data mining search queries may include, for example, the names of drugs with identical contraindications, the most common drugs with back orders in a particular field, trends in particular medical inventory usage, and limitless other information that can be analyzed from the characteristics of use related to safety of each medical item stored in database 504. In this way, any user of the data mining system 155, whether the user is a pharmacy technician, a manufacturer, a distributor, a pharmaceutical company, a healthcare facility, or the like, can analyze trends of choice from encoded information of RFID-tagged medical items in the database.

Figure 18:
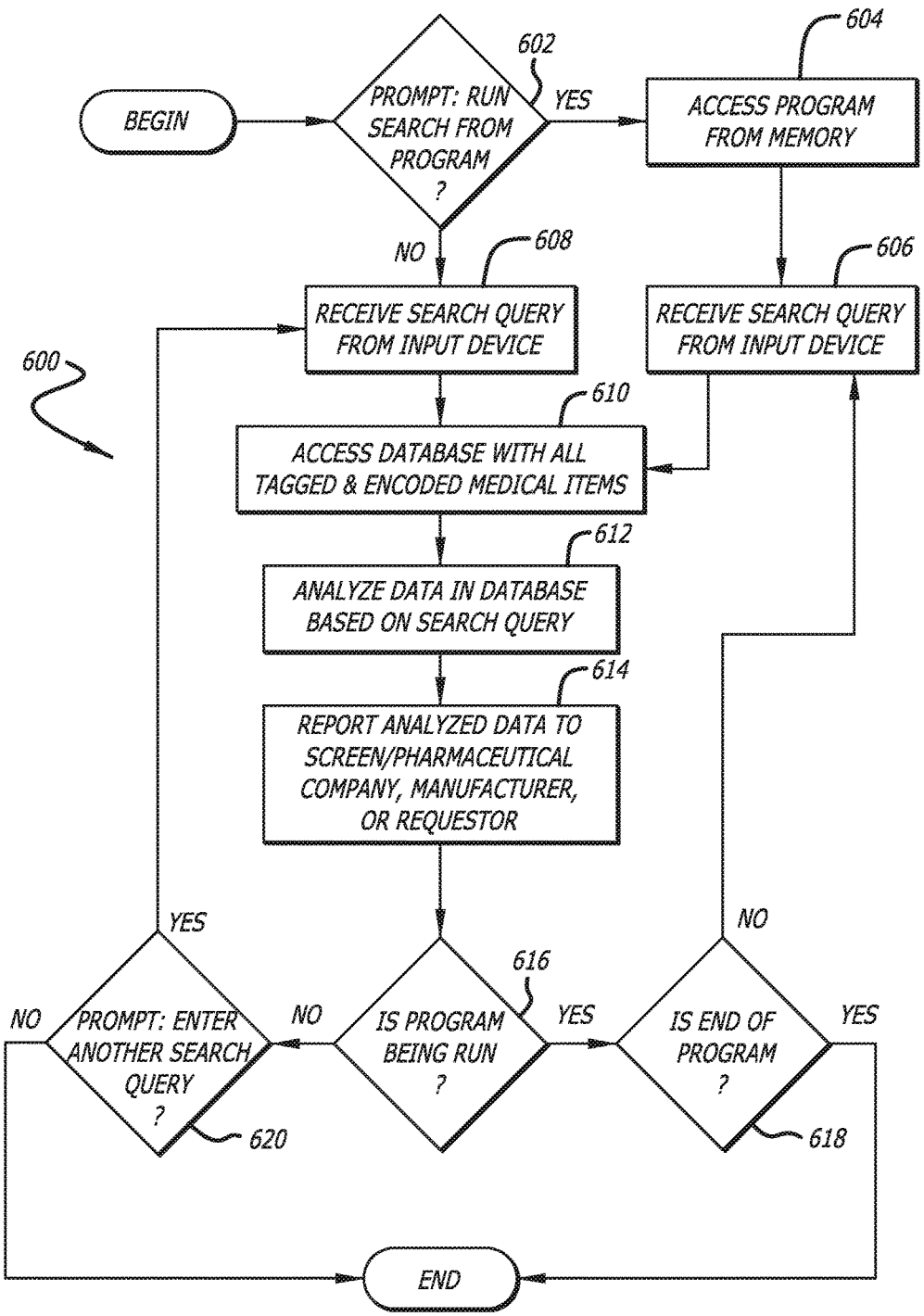
FIG. 18 is a diagram showing a method of mining data in accordance with aspects of the invention in which a data mining search query is received either from the input device or from the list of data mining programming instructions stored in the memory, after which a database with all tagged and encoded medical items is accessed, data from the database is analyzed based on the search query, and the analyzed data is reported.

FIG. 18 illustrates a method 600 for mining data in system 110 after the RFID-tagged medical items have been encoded and stored in the database. At the beginning of the method, a display device that visually displays content is controlled by a processor to prompt the user, such as a pharmacy technician, to run a search query from a program 602 to mine for and obtain data from the database about characteristics of use related to safety of medical items. If the user submits YES, or otherwise answers an equivalent to YES to this prompt, then the processor accesses a program or list of data mining instructions in memory 604 and receives the first search query from the program 606. Alternatively, if the user submits NO, or otherwise answers an equivalent to NO in response to the prompt, then the user is further prompted to manually submit a search query using an input device 608.

Once the search query is received by the processor, either from the input device manually or from the list of data mining instructions in memory, the processor accesses the database with all the identifying information of the tagged and encoded medical items 610. Afterwards, the processor analyzes the information received from the database based on the search query 612. For example, if the search query is, as illustrated in FIG. 17, the most encoded drugs with contraindications, then the processor identifies all the drugs in the database with contraindications, and sorts those results to determine the maximum number of drugs having contraindications. Once the data is analyzed, the data is reported to the user 614. For example, the analyzed data is displayed on the display device such as a screen in the case of local users in the healthcare facility such as pharmacy technicians; alternatively, the analyzed data is transmitted outside the healthcare facility via a communications interface if the user is remote from the healthcare facility, for example, in the case of a pharmaceutical company, manufacturer, or distributor.

After the data is analyzed and reported, the processor checks if the search queries are being received from the program or the input device 616. If the processor determines the search queries are being received from the program, then the processor checks if the most recently run search query is the last search query in the program 618. If more search queries remain in the program to be run, then the processor receives the next search query from the program and repeats the process above beginning at step 606. Otherwise, if the processor determines that the end of the program has been reached and there are no more search queries left on the list, then the process ends. On the other hand, if the processor determines the search query was received manually from an input device, then the processor controls the display device to prompt for another data mining search query 620. If the user answers YES or otherwise states the equivalent of YES using the input device, then the processor receives the user's new search query and the process above repeats beginning at step 608. Alternatively, if the user indicates NO or otherwise states the equivalent NO, then the process ends.

Figure 19:
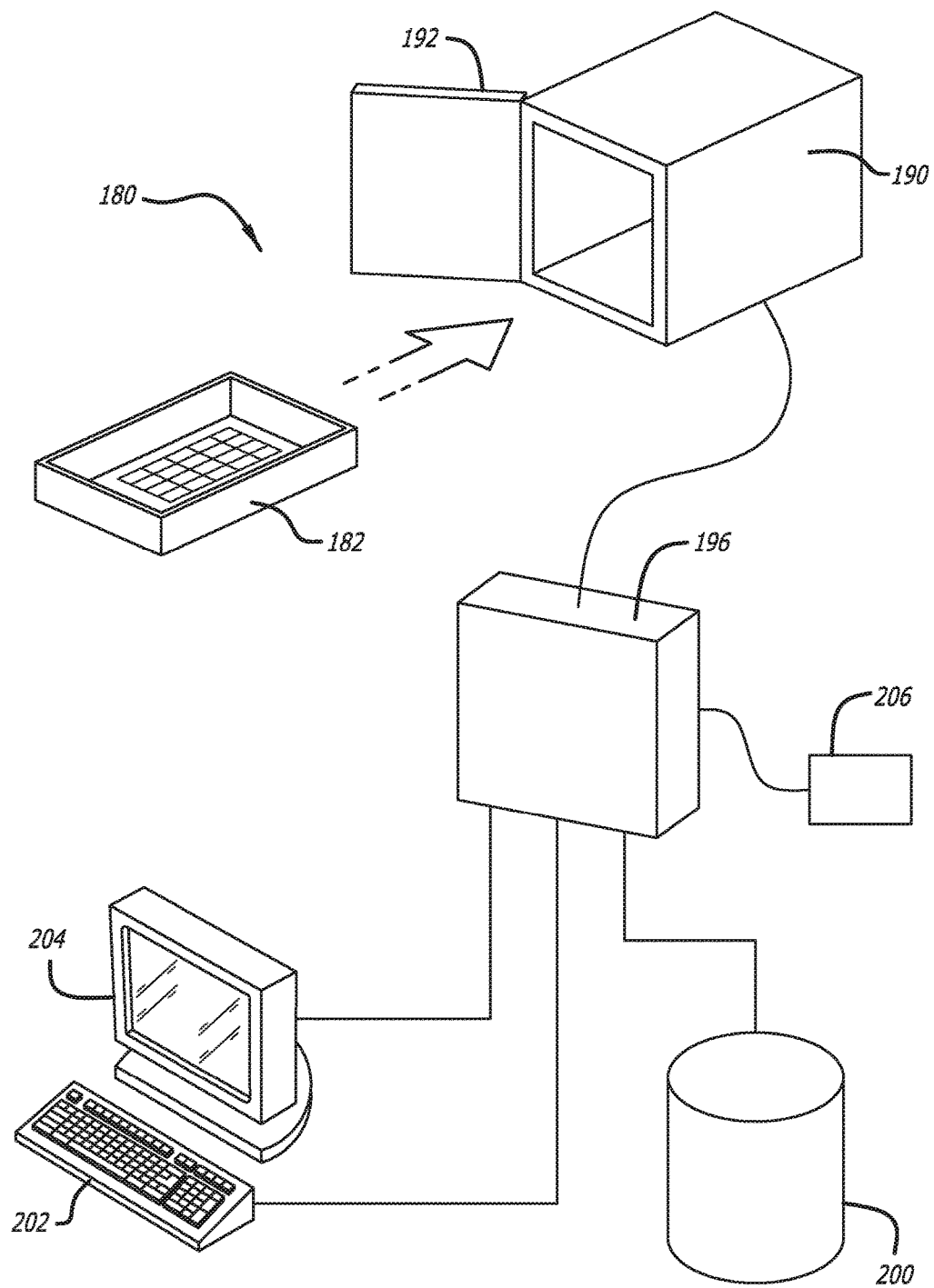
FIG. 19 is a block diagram of a bulk encoding system in which a plurality of blank RFID tags are encoded simultaneously; i.e., in bulk prior to being attached to respective and identical medical items.

In an alternative embodiment as shown in FIG. 19, loose RFID tags, either read-only or writable, may be placed in a tray 182 (see FIG. 11), and encoded in bulk for use with a particular medical item as described above. However in this embodiment, the encoding is performed prior to the RFID tags being affixed to respective medical items. The RFID tags in this embodiment would be assigned to a particular medical item in the database when encoded. After the encoding of the RFID tags has been completed, the RFID tags may then be attached to their assigned medical items when the opportunity permits.

Although the embodiments described herein discuss attaching an RFID tag by means of clear adhesive tape, other means may be used depending on the configuration of the medical items to which they are to be attached. For example, a plastic loop placed around particular medical items may perform the attaching function of the RFID tag to the medical item. In the case of intravenous bags of liquid, the RFID tag may be attached by means of a twist tie to the portion of the bag that is used for hanging the bag from a stand. Other techniques for "attaching" are possible.

As used herein, "packaging configuration" can encompass powder form as well as diluent form of medicines, as well as many other packaging forms.

Although described in embodiments herein as a healthcare facility receiving medical items, other embodiments are possible. Bulk encoding as described herein may be found useful by manufacturers of medical items, by repackagers of medical items, and by distributors of medical items. Items other than medical items may also be tracked using aspects of the invention described herein.

"Serial number" may comprise a string of characters that includes both numbers and letters, or other symbols that are computer readable.

"Healthcare facility" is meant in the broad sense and can include any location where healthcare is administered and where the automated tracking of medical items is performed. This can include assisted living facilities, hospitals, local emergency care clinics and others.

"Characteristic related to safety of use" means any characteristic of the item that could harm a patient to whom it is administered and includes expiration date, name of the medical item, NDC, lot number, dose, concentration, and other characteristics. However, the color of a medical item may or may not be a characteristic that is related to safety of use.

"Blank RFID tag" means an RFID tag that has no human-readable information printed on the tag that relates to a characteristic of the medical item to which it is attached. For example, an RFID tag may have the last six characters of its computer readable serial number printed on the RFID tag but this is still considered to be a blank "RFID tag" because those last six characters do not related to characteristics of the medical item. Similarly, an RFID tag may have a logo printed on the RFID tag but this is also still considered to be a blank RFID tag because the logo does not relate to characteristics of the medical item.

"NDC" means National Drug Code which is a unique product identifier used in the United States for drugs intended for human use.

"Reading the RFID tag" means exciting the electrical circuitry of the RFID tag so that it electrically transmits its serial number so that it can be read.

Although RFID tags are used herein as an embodiment, other data carriers that communicate through electromagnetic energy and transmit serial numbers may also be usable and may be considered to be equivalents.

Unless the context requires otherwise, throughout the specification and claims that follow, the word "comprise" and variations thereof, such as, "comprises" and "comprising" are to be construed in the normal patent law sense; i.e., an open, inclusive sense, which is as "including, but not limited to."

While the present invention has been described herein in terms of certain preferred embodiments, those skilled in the art will recognize that modifications and improvements may be made without departing from the scope of the invention. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A method for bulk encoding a plurality of medical items with respective individual wireless identification tags for identifying and tracking the medical items, each medical item of the plurality having a characteristic that is identical to all other medical items in the plurality and each of the plurality of medical items having a human-readable label located on an outside surface, the encoding method comprising:

storing information about the plurality of medical items, including the identical characteristic in a computer-readable database located in a non-volatile memory;

attaching a wireless identification tag to the outer surface of each of the plurality of medical items with a clear material held by adhesive, each of the attached wireless identification tags having a different serial number, whereby the human-readable label of the medical item is readable when the wireless identification tag is attached;

after the wireless identification tags have been attached to the plurality of medical items, placing all the plurality of tagged medical items into a reading enclosure and then, activating and reading the wireless identification tags while they are attached to their respective medical items to obtain the serial number of each of the wireless identification tags of the plurality of medical items in the same enclosure; and associating the serial numbers read from the plurality of activated wireless identification tags in the enclosure to the characteristic in the database thereby uniquely identifying each of the plurality of medical items with their wireless identification tag serial number.

2. The method for bulk encoding a plurality of medical items of claim 1 wherein the human-readable label of each of the plurality of medical items includes human-readable information that describes a characteristic of the medical item, the bulk encoding method further comprising attaching the clear material of the wireless identification tag to the medical item in a way that the wireless identification tag does not obscure the human-readable information on the human-readable label.

3. The method for bulk encoding a plurality of medical items of claim 1 wherein the plurality of medical items all have the same name
and have an identical characteristic relating to safety of use; and
the step of storing information comprises storing the name and characteristic related to safety of use that is identical for all the plurality of received medical items.

4. The method for bulk encoding a plurality of medical items of claim 3 wherein the step of associating comprises first checking that all names and characteristics of the plurality of received, tagged, and database-entered medical item information of all the plurality of medical items are the same before associating each of the read wireless identification tag serial numbers to the information stored in the database.

5. The method for bulk encoding a plurality of medical items of claim 3 further comprising examining all the plurality of medical items to determine if they are all identical to each other and if it is determined that they are all identical to each other, then performing the reading step.

6. The method for bulk encoding a plurality of medical items of claim 3 wherein the step of reading the wireless identification tag while attached to the medical item further comprises writing information about the medical item to which the wireless identification tag is attached to the wireless identification tag.

7. The method for bulk encoding a plurality of medical items of claim 3 wherein the characteristic related to safety of use comprises at least one of concentration of the medical item, expiration of the medical item, dose of the medical item, and contraindications of the medical item.

8. The method for bulk encoding a plurality of medical items of claim 1 further comprising the step of accessing the database, analyzing information stored in the database based on a mining search query, and once the information is analyzed, reporting data resulting from the analysis.

9. A method for bulk encoding a plurality of medical items with RFID tags for identifying and tracking the medical items, comprising:
selecting a plurality of identical medical items, each of which has a name and a characteristic related to safety of use of the medical item and attaching a blank RFID tag to each of the selected identical medical items, each of the RFID tags having a serial number;
storing information about the selected medical items, including the name and the characteristic related to safety of use in a computer-readable database located in a non-volatile memory;
after the blank RFID tags have been attached to all the identical medical items, reading the blank RFID tags of all the selected medical items at the same time to obtain the serial numbers of the RFID tags; and
associating the serial numbers read from all the blank RFID tags of the identical medical items to the name and characteristic related to safety for that medical item stored in the database thereby identifying that medical item with the serial numbers of the read RFID tags.

10. The method for bulk encoding a plurality of medical items with RFID tags of claim 9 wherein the step of selecting further comprises selecting the medical items with each item having a human-readable label attached to it, the human-readable label including information that describes characteristics related to safety of use of the medical item, the bulk encoding method further comprising attaching the RFID tag to the medical item in a way that does not obscure the human-readable information on the human-readable label.

11. The method for bulk encoding a plurality of medical items with RFID tags of claim 10 wherein the step of attaching the RFID tags to the medical items comprises attaching the RFID tags to the medical items with a clear material wherein the clear material is held with adhesive over at least part of the information of the human-readable label thereby allowing the information to be read through the clear material wherein the human-readable information is not obscured.

12. The method for bulk encoding a plurality of medical items with RFID tags of claim 9 wherein the step of associating comprises checking that the names and characteristics related to safety of use of all of the plurality of identical received and RFID-tagged medical items are indeed identical and are correctly entered into the database before associating each of the read RFID tag serial numbers to the information stored in the database.

13. The method for bulk encoding a plurality of medical items with RFID tags of claim 9 further comprising examining all selected medical items to determine if they are all identical to each other and if it is determined that they are all identical to each other, then performing the reading step.

14. The method for bulk encoding a plurality of medical items with RFID tags of claim 9 wherein the characteristic related to safety of use comprises at least one of concentration of the medical item, expiration of the medical item, dose of the medical item, and contraindications of the medical item.

15. The method for bulk encoding a plurality of medical items with RFID tags of claim 9 further comprising the step of accessing the database, analyzing information stored in the database based on a mining search query, and once the information is analyzed, reporting data resulting from the analysis.

16. A system for bulk encoding a plurality of medical items to track the medical items, at least one of the medical items having a human-readable label affixed to the medical item, the human-readable label having printed information that describes a characteristic of the medical item, the system comprising:
a blank RFID tag attached to each of the medical items to be bulk encoded, each blank RFID tag having a different serial number;
wherein each blank RFID tag has no human-readable information located thereon that is related to a characteristic related to safety of use of the medical item to which the blank RFID tag is attached;
a nonvolatile memory device in which is stored a database of information including a name and a characteristic related to safety of use of each of the plurality of medical items to be bulk encoded;

a container having a size large enough to hold a plurality of identical medical items for bulk encoding;

an RFID reader having an interior reading space that is large enough to receive the container holding a plurality of identical medical items, the RFID reader configured to transmit activation energy to the RFID tags attached to the medical items in the container in response to receipt of a read control signal and that reads the serial numbers of all the RFID tags transmitted by the RFID tags in response to the receipt of the activation energy, the RFID reader providing the received serial numbers; and a processor programmed to communicate a read control signal to the RFID reader to have the RFID reader read all the RFID tags attached to the identical medical items in the tray, and the processor further programmed to receive the serial numbers of the read RFID tags and to control the memory to associate and store the received serial numbers in the data base in relation to the stored names and characteristic of all the identical medical items.

17. The system for bulk encoding a plurality of medical items of claim 16 further comprising clear material with adhesive configured to attach each RFID tag to its respective medical item so that the clear material is placed over the human-readable label without obscuring the information on the human-readable label.

18. The system for bulk encoding a plurality of medical items of claim 16 wherein the processor is further programmed to prompt a user on a display to check that the names and characteristics of all of the plurality of identical RFID-tagged medical items are indeed identical and are correctly entered into the database before associating each of the read RFID tag serial numbers to the information stored in the database.

19. The system for bulk encoding a plurality of medical items of claim 16 wherein the processor is further programmed to prompt a user on a display to examine all of the plurality of identical medical items to determine if they are all indeed identical to each other prior to controlling the RFID reader to read the RFID tags on all of the selected and tagged medical items.

20. The system for bulk encoding a plurality of medical items of claim 16 wherein the characteristic related to safety of use comprises at least one of concentration of the medical item, expiration of the medical item, dose of the medical item, and contraindications of the medical item.

21. The system for bulk encoding a plurality of medical items of claim 16 wherein the processor is further programmed to access the database, analyze information stored in the database based on a mining search query, and once the information is analyzed, report data resulting from the analysis.

* * * * *